US012569142B2

(12) United States Patent
Holzwarth et al.

(10) Patent No.: US 12,569,142 B2
(45) Date of Patent: Mar. 10, 2026

(54) METHOD AND SYSTEM FOR CONTEXT-AWARE PHOTOACOUSTIC IMAGING

(71) Applicant: Deutsches Krebsforschungszentrum Stiftung des oeffentlichen Rechts, Heidelberg (DE)

(72) Inventors: Niklas Holzwarth, Heidelberg (DE); Kris Dreher, Heidelberg (DE); Melanie Schellenberg, Heidelberg (DE); Jan-Hinrich Nölke, Dossenheim (DE); Janek Gröhl, Mannheim (DE); Lena Maier-Hein, Heidelberg (DE)

(73) Assignee: Deutsches Krebsforschungszentrum Stiftung des öffentlichen Rechts, Heidelberg (DE)

( * ) Notice: Subject to any disclaimer, the term of this patent is extended or adjusted under 35 U.S.C. 154(b) by 344 days.

(21) Appl. No.: 18/004,689

(22) PCT Filed: Jul. 15, 2021

(86) PCT No.: PCT/EP2021/069855
§ 371 (c)(1),
(2) Date: Jan. 9, 2023

(87) PCT Pub. No.: WO2022/013397
PCT Pub. Date: Jan. 20, 2022

(65) Prior Publication Data
US 2023/0248244 A1 Aug. 10, 2023

(30) Foreign Application Priority Data
Jul. 15, 2020 (EP) ..................................... 20186038
Aug. 27, 2020 (EP) ..................................... 20193102

(51) Int. Cl.
*A61B 5/00* (2006.01)

(52) U.S. Cl.
CPC .................................. *A61B 5/0095* (2013.01)

(58) Field of Classification Search
CPC ... A61B 5/0095; A61B 8/0891; A61B 8/4416; A61B 8/00; A61B 2560/0228;
(Continued)

(56) References Cited

U.S. PATENT DOCUMENTS 8,848,977 B2 9/2014 Bammer et al.

FOREIGN PATENT DOCUMENTS

WO 2013134782 A1 9/2013

OTHER PUBLICATIONS

Thomas Kirchner, Esther Wild, Klaus H. Maier-Hein, Lena Maier-Hein, "Freehand photoacoustic tomography for 3D angiography using local gradient information," Proc. SPIE 9708, Photons Plus Ultrasound: Imaging and Sensing 2016, 97083G (Mar. 15, 2016) (Year: 2016).*
(Continued)

*Primary Examiner* — Pascal M Bui Pho
*Assistant Examiner* — Nicholas A Robinson
(74) *Attorney, Agent, or Firm* — Grossman, Tucker, Perreault & Pfleger, PLLC

(57) ABSTRACT

Disclosed herein are a method and apparatus for photoacoustic imaging (PAI) or ultrasound (US) imaging of biological tissue (18). The method comprises recording 2D-PAI and/or US images (46) of said biological tissue (18), each 2D-PAI or US image (46) being associated with a corresponding image plane (38), providing, prior to recording said 2D-PAI or US images (46) of said biological tissue (18), an optical pattern (28, 40) on or close to a surface of said biological tissue, said optical pattern (28, 40) comprising one or more optical dyes configured for absorbing light at a pattern-characteristic wavelength. The optical pattern (28, 40) is configured such that the location of the image plane
(Continued)

(38) with respect to the optical pattern (28, 40) can be determined at least approximately from said representation of the optical pattern (28, 40) in said 2D-PAI image (46) and/or that the relative location of consecutively taken 2D-PAI images (46) with respect to each other can be at least approximately determined.

40 Claims, 13 Drawing Sheets

(58) Field of Classification Search
CPC .......... A61B 2560/0431; A61B 5/0035; A61B 5/0073; A61B 5/0075; A61B 5/0077
See application file for complete search history.

(56) References Cited

OTHER PUBLICATIONS

International Search Report and Written Opinion from corresponding PCT Appln. No. PCT/EP2021/069855, dated Oct. 19, 2021. 21 pages.

Chen, T K et al: "A Real-Time Freehand Ultrasound Calibration System with Automatic Accuracy Feedback and Control", Ultrasound in Medicine & Biology, New York, NY, US, vol. 35, No. 1, Jan. 1, 2009, pp. 79-93.

Horvath et al: "Towards an Ultrasound Prove with Vision: Structured Light to Determine Surface Orientation", NCS 7264, 2012, pp. 58-64.

Kirchner Thomas et al: "Freehand Photoacoustic Tomography for 3D Angiography using Local Gradient Information", Progress in Biomedical Optics and Imaging, SPIE—International Society For Optiacal Engineering, Bellingham, WA, US, vol. 9708, Mar. 15, 2016, pp. 97083G-97083G.

Mercier etal: "A Review of Calibration Techniques for Freehand 3-D Ultrasound Systems", Ultrasound in Med. & Biol., vol. 31, No. 2, 2005, pp. 143-165.

Mozaffari et al.: "Freehand 3-D Ultrasound Imaging: A Systematic Review", Ultrasound in Medicine and Biology, New York, NY, US, vol. 43, No. 10, Jul. 14, 2017, pp. 2099-2124.

Rafii-Tari Hedyeh at al: "Panorama Ultrasound for Guiding Epidural Anesthesia: A Feasibility Study", LNCS 6689, 2011, pp. 179-189.

* cited by examiner

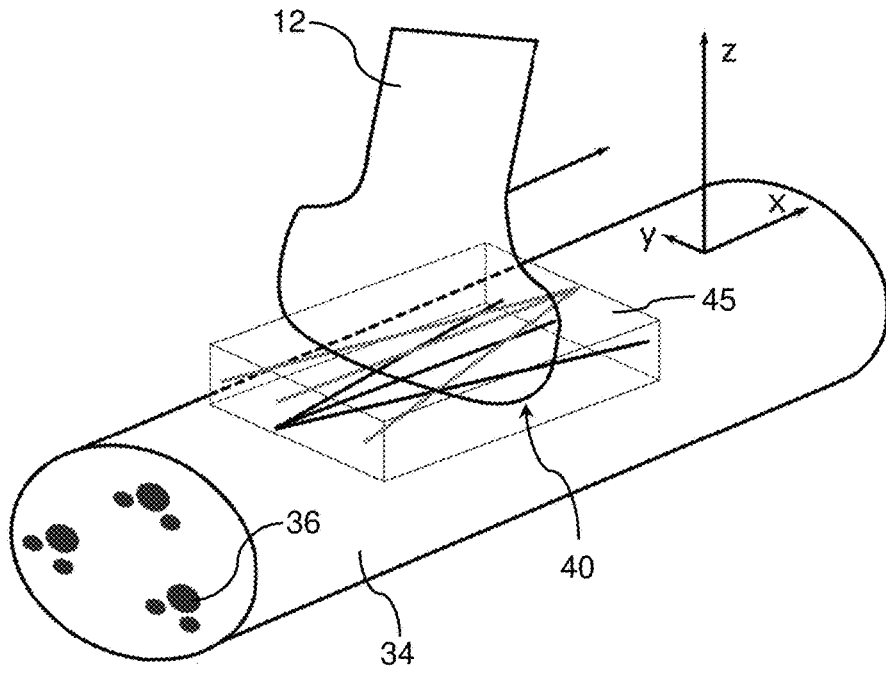
Fig. 12
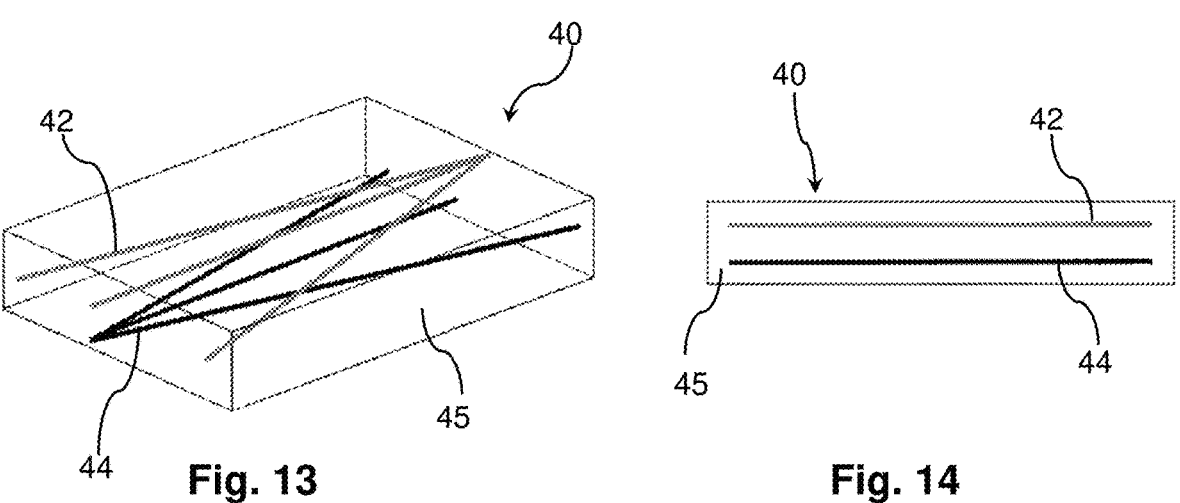
Fig. 13
Fig. 14

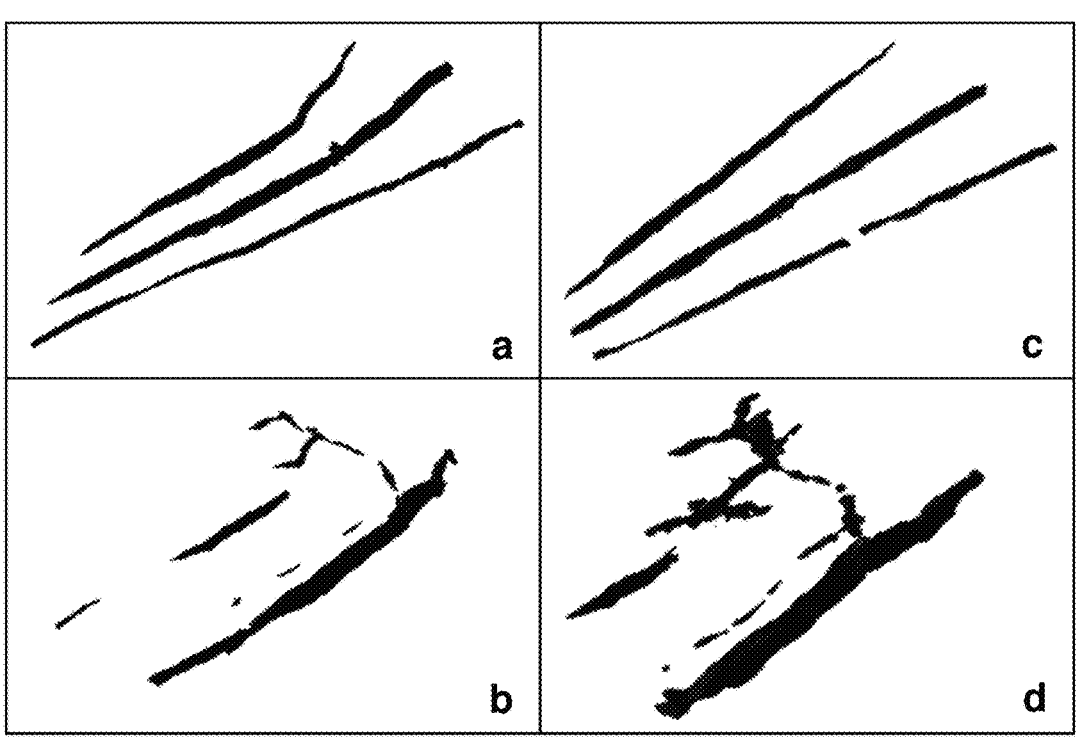
Fig. 17
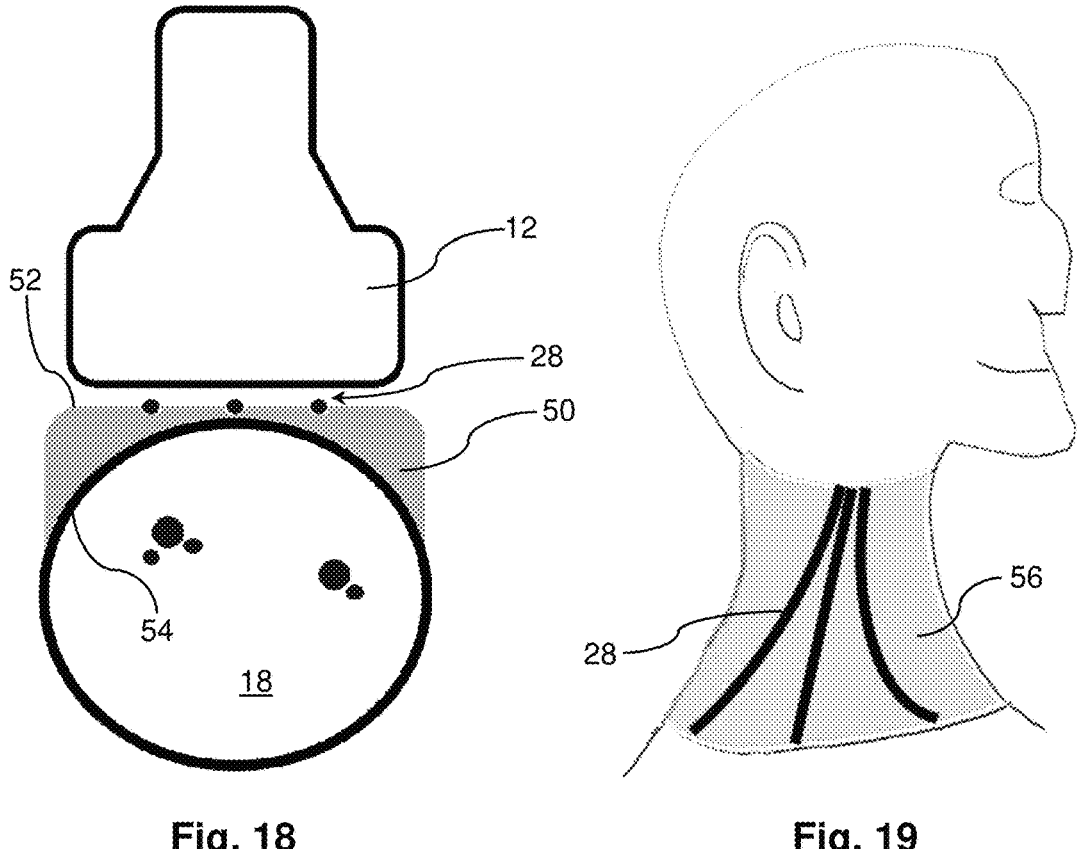
Fig. 18            Fig. 19

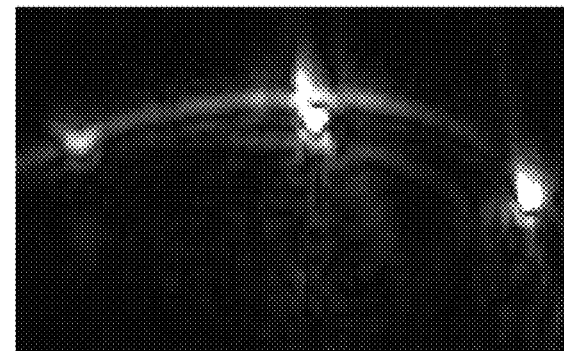
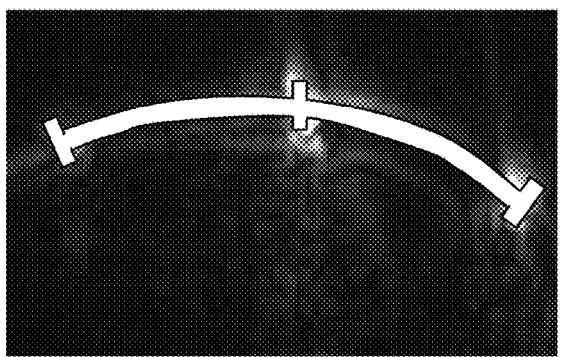
Fig. 20
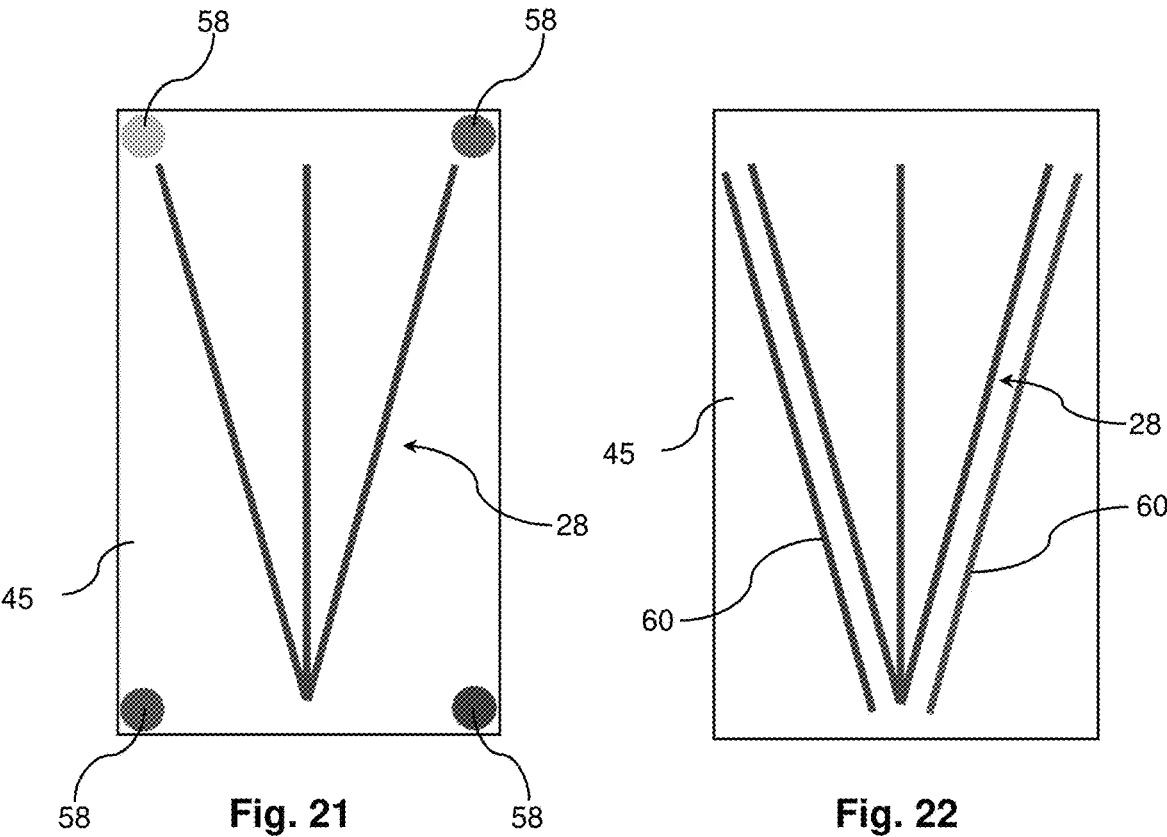
Fig. 21
Fig. 22

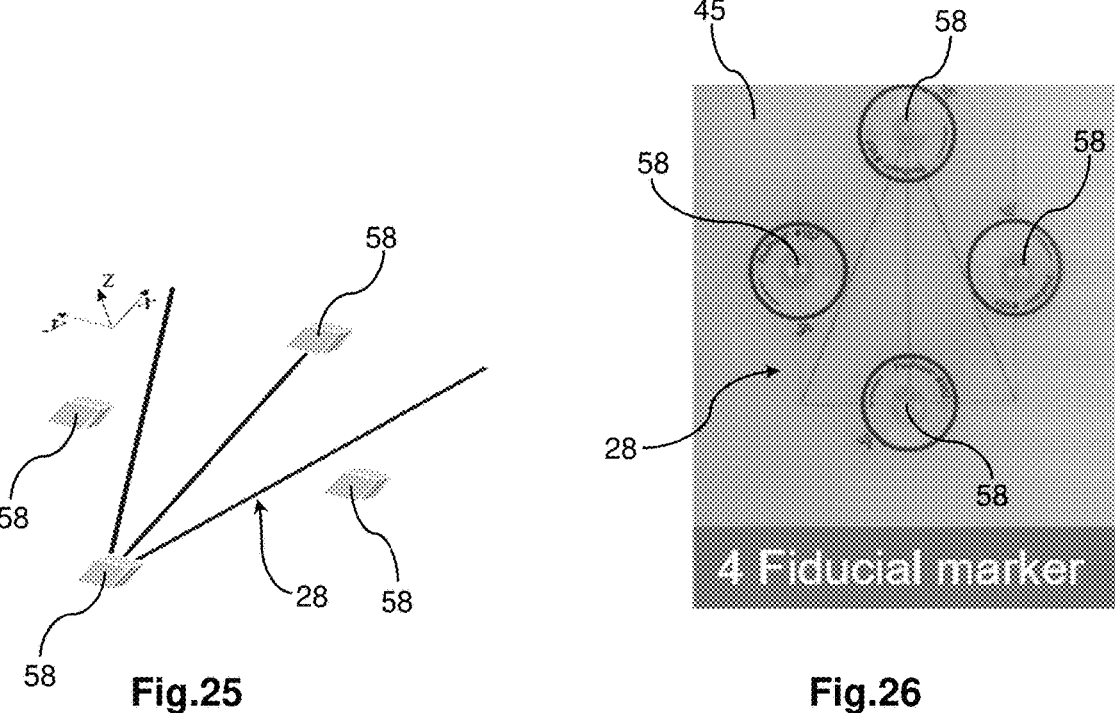
Fig.25
Fig.26
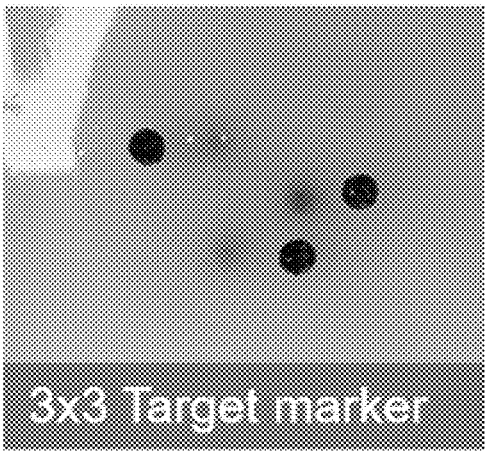
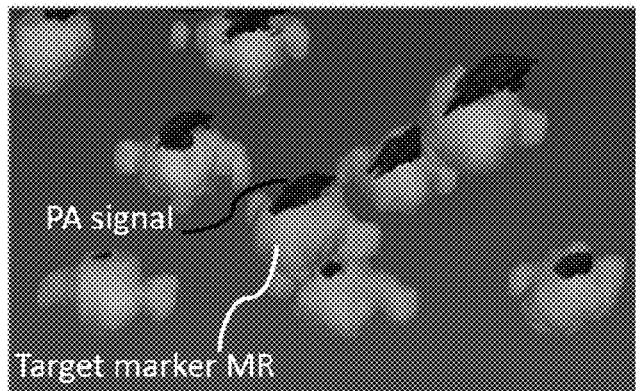
Fig.27
Fig. 28

METHOD AND SYSTEM FOR CONTEXT-AWARE PHOTOACOUSTIC IMAGING

FIELD OF THE INVENTION

The present invention is in the field of biological or medical imaging. In particular, the present invention relates to a method and system for context-aware photoacoustic or ultrasound imaging.

BACKGROUND OF THE INVENTION

Photoacoustic imaging (PAI) is a novel imaging modality that enables both, morphological and functional tissue imaging in depths up to several centimeters. In PAI, non-ionizing and typically multispectral light pulses are delivered into a medium, such as a biological tissue of interest. Some of the delivered light energy will be absorbed and converted into heat, leading to transient thermoelastic expansion and thus wideband ultrasonic emission. The generated pressure waves, typically ultrasonic waves are received by ultrasonic transducers which allow for converting the received ultrasonic waves into electrical signals. The electrical signals can then be processed into images, which correspond to a representation of the space-resolved absorption of the light pulses in the tissue. Simply put, the magnitude of the ultrasonic emission, or in other words, the photoacoustic signal, which is proportional to the local energy deposition by light absorption, reveals physiologically specific absorption contrast. This physiologically specific absorption contrast may expose anatomic structures, but also functional tissue parameters, for example blood oxygenation, the distinction of cancerous tissue from noncancerous tissue or the like.

Key advantages of PAI, especially compared to other functional imaging modalities, are safety due to use of non-ionizing radiation, high spatial resolution, cost-efficiency and also a comparatively straightforward clinical workflow integration. Clinical applications are manifold, ranging from the staging of Crohn's disease to the detection of sentinel lymph nodes and the distinction of healthy tissue and malignant lesions in human breast.

Most PAI systems, however, only deliver 2D image slices, representing a sectional image plane within the tissue. Various 2D image slices can be recorded while moving e.g. a handheld PAI probe across the surface of a target tissue, typically the skin of a body part, thereby covering a three-dimensional volume, but the individually recorded 2D image slices do not have a precisely known spatial relation to each other. This makes it difficult to render morphological and functional properties in 3D, or to re-target a specific anatomical location with the PAI probe, for example for the purpose of therapy monitoring, because images of the same patient taken at different points in time are commonly not linked to each other.

In order to cope with these deficiencies, PAI probes and processing algorithms have been proposed that allow for recording 3D images from tissue volumes located beneath the probe. However, this does not only require bulkier and costlier PAI probes, but also much higher image processing resources and time, making it difficult to provide images in real time, such as at a video frame rate.

Some PAI probes are not only capable of recording PAI images, but also capable of recording ultrasound (US) images. Generally, the same transducers for detecting the acoustic signal of the PAI can also be used for recording ultrasound signals, and the same type of processing of the electrical signals generated by the transducers can be used to construct 2D ultrasound images. Accordingly, additionally providing for US imaging capability does not require much additional hardware and processing expense on the detection side. The main difference between PAI and US is the source of the acoustic signal, namely light absorption in case of PAI and reflection of an acoustic stimulus signal in case of US imaging. Having both functionalities in a same probe is particularly advantageous, as it allows for combining the benefits of both modalities, for example a combination of the well-known anatomical imaging capabilities of US with the functional imaging of tissue facilitated by PAI. With respect to the US modality, the same limitations with respect to the lack of known spatial relationship between individual 2D US images exist as in case of PAI.

SUMMARY OF THE INVENTION

The problem underlying the present invention is therefore to provide a method and system for photoacoustic and/or US imaging of biological tissue that allows for improving the information conveyed by simple, unrelated 2D-PAI or US images with moderate apparatus expenditure and increase in operational complexity. This problem is solved by a method according to claim 1 and a system according to claim 9. Preferred embodiments are defined in the dependent claims.

According to a first aspect of the invention, a method of photoacoustic imaging (PAI) of biological tissue, in particular a body part, is provided. The method comprises steps of recording 2D-PAI and/or US images of said biological tissue, each 2D-PAI or US image being associated with a corresponding image plane.

Moreover, the method further comprises providing, prior to recording said 2D-PAI or US images of said biological tissue, an optical pattern on or close to a surface of said biological tissue, said optical pattern comprising one or more optical dyes configured for absorbing light at a pattern-characteristic wavelength. Herein, the term "dye" has a broad meaning and may denote any substance capable of absorbing light in a predetermined wavelength range.

The method further comprises recording 2D-PAI images using pattern-imaging light pulses having a pattern-characteristic wavelength for which the absorption by said one or more dyes is sufficiently high such that said optical pattern is visibly represented in said 2D-PAI images. Herein, said optical pattern may be configured such that the location of the image plane with respect to the optical pattern can be determined at least approximately from said representation of the optical pattern in said 2D-PAI image. In addition or alternatively, the optical pattern may be configured such that the relative location of consecutively taken 2D-PAI images with respect to each other can be at least approximately determined from said representation of the optical pattern in said consecutive 2D-PAI images.

The method further comprises determining one or both of
- the location of the image plane of each given 2D-PAI or US image of said biological tissue with respect to the optical pattern, and
- the relative location of consecutively taken 2D-PAI or US images from the representation of the optical pattern in said given 2D-PAI image(s), or in one or more 2D-PAI images recorded while a PAI probe used for recording the images is in the same position or a position close to the position in which the given 2D-PAI or US image(s) of said biological tissue is recorded.

Note that without further mention, the order in which the method steps are mentioned in the claims and this summary does not imply a specific order in which they are to be carried out. Instead, any order that is technically feasible may be part of the claimed invention.

According to this aspect of the invention, the PAI relies on recording of 2D-PAI images, thereby benefiting from the lower hardware and image processing demand. However, according to the invention, a spatial relationship between individual 2D-PAI images of the biological tissue can be established, which is missing in current 2D-PAI approaches, and which can be exploited e.g. to construct 3D images from a plurality of 2D-PAI images. The spatial relationship between individual 2D-PAI images of the biological tissue may in one variant of the invention be established via the spatial relationship of each of the individual 2D-PAI images with respect to the optical pattern that is provided on or close to a surface of the biological tissue and hence acts as a spatial reference for each of the 2D-PAI images.

However, in another variant, the spatial relationship between individual 2D-PAI images of the biological tissue may be established by determining, using the optical pattern, the relative location of consecutively taken 2D-PAI images. This variant does not require that an explicit spatial relationship of the individual 2D-PAI images with respect to the optical pattern is determined.

Importantly, the optical pattern is visibly represented in the same 2D-PAI images as the biological tissue, or at least in one or more 2D-PAI images recorded while the PAI probe is in the same or a similar position as when recording the 2D-PAI or US image of the biological tissue. Note in this regard that a PAI image will often include information obtained with different tissue-characteristic wavelengths, which are typically irradiated into the tissue sequentially, such that the PAI image will include contributions obtained at slightly different points in time. However, the individual wavelength contributions to the 2D image are acquired so quickly one after the other that the position and pose of the PAI probe hardly changes on this short timescale, such that the image slices corresponding to different tissue-characteristic frequencies are for all practical purposes associated with the same image plane within the tissue. Similar considerations apply for recording 2D-PAI images representing the optical pattern, which are obtained with the same apparatus and the same imaging technique, except that pattern-imaging light pulses at one or more dedicated "pattern-characteristic" wavelength(s) are applied, at which the dye included in the optical pattern has sufficient absorption such that the optical pattern becomes visible in the 2D-PAI image.

Accordingly, the optical pattern may in some embodiments be represented in the same "multispectral" 2D-PAI images as the biological tissue, and the location of the image plane of this 2D-PAI image with respect to the optical pattern can then be determined from the representation of the optical pattern in this image. In the alternative, dedicated 2D-PAI images can be recorded using pattern-imaging light pulses and hence only or predominantly showing representations of the optical pattern, and from these dedicated 2D-PAI images, the location of the image plane with respect to the optical pattern can be discerned. If these images are recorded very shortly before or after the 2D-PAI or US image of the biological tissue, it can be assumed that the image planes are identical. The accuracy can even be improved by relying e.g. on two dedicated PAI images recorded with the pattern-characteristic wavelengths shortly prior to and after recording the 2D-PAI image of the biological tissue, and then determining the location of the image plane by interpolation of the image planes obtained for these two dedicated PAI images.

Note that due to the two-dimensional imaging modality, the representation of the optical pattern in any 2D-PAI image will amount to a sectional view of the optical pattern only. However, as will be demonstrated with reference to specific examples below, using suitable optical patterns, it is nevertheless possible to determine the location of the image plane with respect to the optical pattern at least approximately from this sectional view alone.

As the skilled person will appreciate, as compared to the simple prior art PAI setups, the invention merely requires providing an additional optical pattern and pattern-imaging light pulses, but no further navigation or imaging modality has to be employed to obtain the additional information regarding the spatial relationship of the individual 2D-PAI images. Instead, the method relies on the ordinary PAI equipment and procedure, except that a light source for the pattern-characteristic wavelength has to be provided, if this wavelength is different from any of the tissue-characteristic wavelengths used for the tissue-imaging light pulses. Whether or not an additional pattern-characteristic wavelength for imaging of the optical pattern has to be employed or not ultimately depends on the absorptivity of the dye used for the optical pattern. In many cases, it is advantageous if this dye has no or only very little absorptivity at any of the tissue-characteristic wavelengths, such that it is "invisible" when it comes to imaging the tissue. This implies that the pattern-characteristic wavelength must be different from the tissue-characteristic wavelengths, and that a corresponding light source (or color channel of a tunable light source) has to be provided. However, in simple embodiments, the pattern-characteristic wavelength may be the same as the tissue-characteristic wavelength or one of the tissue-characteristic wavelengths. So while in the following description a distinction between the pattern-characteristic and tissue-characteristic wavelengths is made to discuss the more general case, it should be kept in mind that this always includes the special case where the pattern-characteristic wavelength corresponds to the tissue-characteristic wavelength (or one out of a plurality of tissue and characteristic wavelengths), which also implies that the PAI image of the tissue and of the pattern are acquired simultaneously, without explicit mention.

In a preferred embodiment, recording said 2D-PAI images of said biological tissue comprises
   irradiating tissue-imaging light pulses into said tissue using a PAI probe, said tissue-imaging light pulses having tissue-characteristic wavelengths to be absorbed in said biological tissue,
   receiving ultrasonic waves, in particular ultrasonic waves generated upon absorption of said tissue-imaging light pulses in said tissue using said PAI probe and converting said received ultrasonic waves into electrical signals, and
   constructing 2D images from said electrical signals, said 2D images representing the space-resolved absorption of said tissue imaging-light pulses in a sectional image plane within the tissue.

As the skilled person will appreciate, in PAI, the energy deposition in the tissue is governed by the product of fluence and absorption. However, if the fluence is at least approximately known, information about the space-resolved absorption of the tissue can be obtained by the PAI measurement.

As mentioned above, in some embodiments, said determined location of the image plane of said given 2D-PAI or US image or the established relative location of consecutively recorded 2D-PAI or US images is used for constructing a 3D image from a plurality of 2D-PAI/US images.

In addition or alternatively, the determined location of the image plane of said given 2D-PAI/US image may be used for targeting a specific anatomical location at different points in time, provided that the optical pattern remains in place, or can be arranged at the exact same location than at a previous point in time.

In some embodiments, the determined location of the image plane may be used for registering the 2D-PAI image with imaging data obtained with another imaging modality. Examples of other imaging modalities are CT, NMR and multispectral imaging. For this purpose, the optical pattern can be extended to include contrast agents for these imaging modalities, as will become more apparent from examples below.

Extending the optical pattern to include contrast agents for other imaging modalities (e.g. CT or NMR), referred to as "additional contrast agents" in the following, could mean to permanently provide the optical pattern and the additional contrast agents on a same carrier, such as a plastic foil. However, in other embodiments, the additional contrast agents may only be temporarily provided on the same carrier for the time of recording images with said other imaging modality, or directly on the skin. In some embodiments, markers or other aids for placing the additional contrast agents at predetermined positions with respect to the optical pattern are provided. Such marker or other aid could be provided by portions of the optical pattern, or be provided on a carrier that is also carrying the optical pattern. In preferred embodiments, this marker or aid is printed on the carrier using an ink that has no or only little absorptivity at the pattern-characteristic and/or tissue-characteristic wavelengths. Note that as used herein, the term "(additional) contrast agent" is to be understood in a broad manner and merely refers to its function of being discernible in a medical image, irrespective of its physical shape or a mechanical structure. For example, the "additional contrast agents" may be formed by individual fiducial markers that can be releasably attached to the same carrier on which said optical pattern is provided.

Only temporarily providing for the additional contrast agents may have various advantages. One advantage is that in this case, the additional contrast agents can be of very different kinds, as they need not be specifically selected to be optically or physically compatible with the PAI imaging. If they are removable, they will not interfere with the PA imaging procedure. Also, the additional markers could be reused for other patients.

Note that in some embodiments, a plurality of sets of PAI images taken at different points in time are co-registered with the same image recorded with said other imaging modality. For example, it may be sufficient to record one medical image of said other imaging modality at the beginning of an extended treatment, for example to obtain anatomical or morphological information at very high resolution. In the course of the treatment, various sets of PAI images can be recorded at different times, for example to monitor functional parameters over time, while the anatomy of the patient as derived with the aid of the other imaging modality does not change. For example, only one (typically costly and time-consuming) NMR image can be taken at the beginning of the treatment or monitoring period and then correlated with a multitude of sets of PAI images taken over the course of days or even weeks, where the PAI images can be generated quickly and at low cost as needed. In such a scenario, the optical pattern could remain attached to the patient for an extended period of time, and it would be advantageous to be in a position to remove the additional contrast agent once they are no longer needed. Moreover, it is not even necessary that the optical pattern itself remains attached to the patient. It would also be sufficient if there is a universal marker remaining on the skin that would allow to attach the optical pattern or an identical copy thereof at the same, reproducible position at a later point of time. This universal marker could then also be used as a reference for the aforementioned additional contrast agents. For example, both, the optical pattern and the additional contrast agents could each be provided on a corresponding plastic foil that can each be arranged in a predetermined position with respect to the universal marker. More generally, a universal marker could be provided on the patient with a known pose relative to all modality specific markers (including the optical pattern and e.g. fiducials for CT or NMR imaging).

In some embodiments, the PAI and/or the imaging modality that is registered with the PAI is used for obtaining a semantic representation of the imaged volume. Herein, a semantic representation involves an understanding of each pixel, of groups of pixels, or of at least part of the pixels of the PAI image with regard to high-level semantics, e.g. spatial, functional and semantic relations. One aspect of such semantic representation may be what is often referred to as "semantic image segmentation" i.e. labelling pixels of an image with a corresponding class of what is being represented. For example, each pixel of the PAI image could be labelled as to whether it is part of a vessel or some tissue outside the vessel. Higher-level semantics could for example comprise information such as the radius of the vessel, the type of vessel, information with regard to the hierarchical position of the vessel as a branch in a vessel tree and the like. This semantic representation of the imaged volume can often be best obtained by combining the PAI images with information obtained from said other imaging modality.

Note that the semantic representation can further be used to refine the multi-modal registration. For example, first a rough alignment of images could be obtained with fiducials, which could then be refined by e.g. deforming the 2D-PAI slices in the reference coordinate system so that certain structures as reflected in the semantic representation (e.g. skin, vessels or other structures) match. This deformation can for example become necessary in order to account for a physical deformation that occurs during recording the PAI images, for example due to the contact pressure of the PAI probe on the body part. In a similar manner, the semantic representation can be used to adjust the aforementioned angle between the image plane and the at least one pattern plane.

While PAI—due to its inherent spectroscopical character—is particularly suitable for obtaining functional or physiological information, and in particular information related to the concentration of certain molecules or substances (e.g. water, hemoglobin, collagen, or dyes associated with targeted markers), when it comes to morphological details, other imaging modalities, in particular CT and NMR, are often superior, and they can be used for deriving or establishing the aforementioned semantic representation.

However, in other embodiments, the semantic representation is generated based on the PAI images alone, e.g. using a machine learning algorithm that has been trained based on PAI images in combination with co-registered images of other imaging modalities, the latter serving as ground truth during the machine learning. For example, such machine learning algorithms may be supervised deep learning-based algorithms, preferably algorithms based on a U-net or based on a generative adversarial network (GAN).

In some embodiments, the machine learning algorithm has been trained using simulated PA volumes, where the exact tissue topology underlying the simulation serves as ground truth.

In preferred embodiments of the method, the determined location of the image plane of said given 2D-PAI image is used for constructing a 3D PAI image from a plurality of 2D-PAI images, and a semantic representation of the volume covered by said 3D PAI image is derived.

In some embodiments, said semantic representation of the volume covered by said 3D PAI image is derived relying, in addition to said PAI image, on a 3D image of said volume obtained with a different imaging modality, in particular relying on a 3D US, CT or NMR image.

In some embodiments, said semantic representation of the volume covered by said 3D PAI image is derived using a machine learning algorithm that has been trained based on one or both of PAI images in combination with co-registered images of another imaging modality, in particular in combination with co-registered US, CT or NMR images, simulated PA volumes, where the exact tissue topology underlying the simulation serves as ground truth.

Herein, said machine learning algorithm is preferably a supervised deep learning-based algorithm, in particular an algorithm based on a U-net or based on a generative adversarial network (GAN).

In a preferred embodiment, said optical pattern extends in at least one two-dimensional pattern plane, wherein said step of determining the location of the image plane of each given 2D-PAI/US image of said biological tissue with respect to the optical pattern amounts to determining a sectional line along which the image plane of said 2D-PAI/US image and said at least one pattern plane intersect with each other. Note that the difficult part of determining the location of a 2D-PAI/US image with respect to the optical pattern is to determine the geometric plane in which the 2D-image lies, this geometric plane is referred to as the "image plane" herein. Once this image plane is determined, it is easy to determine the position of the image within the image plane with respect to the optical pattern, since the optical pattern is represented in the 2D-PAI/US image.

Moreover, the position of the image plane with respect to the optical pattern can in many applications be defined with sufficient precision by merely specifying the sectional line along which the image plane of said 2D-PAI image and said at least one pattern plane intersect with each other. The missing degree of freedom, i.e. the angle between the image plane and the at least one pattern plane, on the other hand, can often be controlled with sufficient accuracy by other means, as will become apparent from the discussion below, and hence need not necessarily be determined with the help of the optical pattern. Herein, it ought to be acknowledged that both, the tissue and the optical pattern may deform. This means that the optical pattern and the tissue need not be related by a rigid transformation in practice.

In a preferred embodiment, said PAI-probe is placed on the surface of the biological tissue, in particular the skin of a body part such that the 2D-PAI image plane is at least approximately perpendicular to the two-dimensional pattern plane. Note that the expression "placed on the surface" does not imply that the PAI probe must be in direct contact therewith, as in practice there may e.g. be parts of the optical pattern, a carrier structure on or in which the optical pattern is provided, and typically also films of gel or the like in between to allow for acoustic coupling between the tissue and the probe via the optical pattern. If this perpendicular arrangement is ensured, then the location of the "image plane", i.e. the geometric plane in which the 2D-PAI/US image lies, is indeed sufficiently defined by the above the sectional line of said PAI/US image plane and said at least one pattern plane. This perpendicular arrangement can often be insured simply by careful operation of a handheld device, possibly, but not necessarily assisted with some sort of guiding means.

In some embodiments, said optical pattern has a three-dimensional structure, extending in at least one two-dimensional pattern plane and additionally in a thickness direction perpendicular to said pattern plane. In this variant, said step of determining the location of the image plane of each given 2D-PAI/US image of said biological tissue with respect to the optical pattern amounts to determining a sectional plane along which the image plane of said 2D-PAI/US image and said three-dimensional pattern structure intersect with each other. Again, once this geometric plane is determined, it is easy to determine the precise location of the 2D-PAI/US image within this geometric plane with respect to the optical pattern based on the representation of said optical pattern in the 2D-PAI image itself.

There are many possible ways to define the three-dimensional optical pattern such that the aforementioned sectional plane can be uniquely determined from the representation of the optical pattern in the 2D-PAI image alone. In one preferred embodiment, said optical pattern extends in two or more two-dimensional pattern planes spaced from each other in thickness direction, and said step of determining the location of the image plane of each given 2D-PAI/US image of said biological tissue with respect to the optical pattern comprises determining a sectional line along which the image plane of said 2D-PAI/US image and one of said at least two pattern planes intersect with each other, as well as a step of determining an angle between said one pattern plane and said image plane of said given 2D-PAI/US image of said biological tissue based on at least one other of said at least two pattern planes.

Suitable optical patterns may e. g. be any binary 2D pattern in which each intersection line is unique.

In a preferred embodiment, the optical pattern comprises three or more lines generally extending along an extension direction, but also diverging in said extension direction. Herein, said step of recording PAI/US images comprises moving said PAI/US probe along said extension direction and recording said PAI/US images at different positions along said extension direction.

This measurement can be carried out by a physician, but may alternatively be carried out by a robot.

In a related embodiment, said step of determining the location of the image plane of each given 2D-PAI image of said biological tissue with respect to the optical pattern comprises determining a position along said extension direction based on distances between representations of said lines, and in particular based on a sum or an average of distances between representations of said lines in said given 2D-PAI image, or in one or more 2D-PAI images recorded while the PAI probe is in the same position or a position close to the position in which the given 2D-PAI image of said biological tissue is recorded. Moreover, the method preferably further comprises a step of determining an angle between said extension direction and a sectional line of the image plane with a pattern plane in which said three or more lines are arranged, based on distances between representations of said lines, and in particular based on a difference or a quotient of distances between representations of said lines in said given 2D-PAI image, or in one or more 2D-PAI images recorded while the PAI probe is in the same position or a position close to the position in which the given 2D-PAI image of said biological tissue is recorded.

In preferred embodiments, said optical pattern is provided on or in a foil or a cushion or pad to be placed on top of said biological tissue, in particular on the skin of a body part. Such a cushion or a pad preferably has a lower side adapted to or capable of adapting to the surface of the biological tissue, in particular the skin of a body part, and an upper side having a flat surface for placing a PAI probe thereon. The flat surface may assist in placing the PAI probe such that the 2D-PAI image plane is at least approximately perpendicular to the two-dimensional pattern plane, and hence forms an example of the aforementioned guiding means. The cushion or pad may be partially deformable. In some embodiments, the cushion or pad may be in the form of a collar for placing on a person's neck. This is particularly useful for carrying out anatomical and/or functional imaging of lymph nodes, thyroid, parotid gland, other muscles and glandular tissue and the like.

In alternative embodiments, said optical pattern is initially provided on a carrier, and said method comprises a step of transferring said pattern from the carrier to a surface of said biological tissue, in particular to the skin of a body part. For example, the optical pattern may be provided on a front side of a carrier similar to those known from fake tattoos, where the carrier may be placed on the body part with the front side facing the skin, and the backside is moistened and then peeled off the skin, while the optical pattern remains on the skin. This embodiment is particularly useful for revisiting locations that have been previously imaged, e. g. for therapy monitoring purposes or the like.

In a preferred embodiment, the absorptivity of the of the one or more dyes at the corresponding pattern-characteristic wavelength is a factor of 2 higher, preferably a factor of 10 higher than at any of said tissue-characteristic wavelengths. This way, it can be ensured that the optical pattern does not compromise the recording of the tissue images.

In a preferred embodiment, for recording said 2D-PAI images of said biological tissue, at least 2, preferably at least 4, and most preferably at least 6 different tissue-characteristic wavelengths are used. With a larger number of tissue-characteristic wavelengths, more functional parameters can be discerned.

In a preferred embodiment, the pattern-characteristic wavelength is shorter than any of said tissue-characteristic wavelengths.

In a preferred embodiment, the dye is visible in the visible light spectrum. In particular, said dye may be formed by methylene blue or ICG.

In a preferred embodiment, the method further comprises using said optical pattern as a calibration standard for normalizing PAI intensity values. This is particularly useful for quantitative photoacoustic imaging, in which some sort of quantitative measure of the absorptivity of the tissue is determined. An important application for this is functional imaging, such as determining oxygenation or the like, where quantitative absorption is related to functional tissue parameters. Currently, it is also difficult to compare PAI images recorded with different apparatuses in any quantitative way, because signal intensities obtained for the same tissue with different apparatuses will usually differ from each other. Using the optical pattern having a known absorptivity, the signal intensity in the PAI image can be calibrated or normalized, such that quantitative results obtained with different apparatuses can be compared with each other.

In a preferred embodiment, said step of providing said optical pattern on or close to a surface of said biological tissue comprises drawing the optical pattern on the surface of the biological tissue, in particular the skin of a body part, or on a carrier arranged close to said surface of said biological tissue. Indeed, in a simple embodiment of the invention, the pattern can be drawn in a freehand manner, and such a pattern may already assist in determining the relative location of consecutively taken 2D-PAI images, as will be described below. For this, it is not even necessary that the precise shape of the pattern is known, as merely the comparison of the representation of the optical pattern in consecutive 2D-PAI images may give useful information regarding their relative location. However, in a preferred embodiment, the method may further comprise a step of taking a photograph of the drawn optical pattern and using information derived from said photograph in said step of determining the location of the image plane of each given 2D-PAI or US image of said biological tissue with respect to the optical pattern, and/or in the step of determining the relative location of consecutively taken 2D-PAI or US images.

In a preferred embodiment, said step of determining the relative location of consecutively taken 2D-PAI or US images is based on employing a continuity constraint on the representation of the optical pattern in said consecutively taken 2D-PAI images, or in 2D-PAI images recorded while a PAI probe is in the same position or a position close to the positions in which the respective consecutive US images of said biological tissue are recorded. Namely, assuming that the pattern consists of or at least comprises a number of continuous objects, such as continuous lines, the relative location of the consecutively taken 2-D PAI images should be such that the continuity of these continuous objects is ensured. Accordingly, the relative location of the recorded 2D-PAI images can in many cases be determined with sufficient accuracy using an algorithm employing such continuity constraint. For this purpose, for example, a curvy line drawn by hand, possibly including various loops, is very well suited and can be simply established on the surface of the tissue, e.g. the skin of a body part.

In addition or alternatively, the speed of a movement of the a PAI probe with respect to the biological tissue during the imaging process may be determined based on a difference in the representation of the optical pattern in consecutively taken 2D-PAI images. Namely, for any pattern structure that is not parallel to the direction of the movement of the PAI probe, the deviation between the representations of the pattern structure in consecutive 2D-PAI images is the bigger, the higher the speed is. The assessment of this speed can be used for various purposes, for example for assisting the user in carrying out the scan with an approximately constant speed, or for estimating the distance between consecutively taken 2D-PAI images, which for a given constant image rate is proportional to the speed. This distance can for example be used in constructing 3D images.

In a preferred embodiment, regions within said optical pattern can be encoded by one or both of
   using dyes having absorption maxima at different pattern-characteristic wavelengths for different regions within said optical pattern, and
   a visible grid or other type of visible pattern allowing for identifying regions within said optical pattern by visual inspection.

Graphically speaking, dyes having absorption maxima at different pattern-characteristic wavelengths lead to a "color code" of the pattern in the 2D-PAI images, where the color indicates a region within said optical pattern at which the image has been taken. This way, it is easy to at least roughly associate a certain 2D-PAI image with a certain location in the tissue with reference to the optical pattern.

Moreover, the visible grid or other visible pattern can allow the user to easily revisit a position where a 2D-PAI image has been previously taken. For example, the grid can resemble a coordinate system or the like as in a geographic map. Then, when determining the position of a 2D-PAI image with respect to the optical pattern, the coordinates with respect to the visible grid can be established, and the user can find the corresponding location with the probe at a later point in time based on these coordinates. This is particularly useful in cases where the optical pattern remains on the tissue for an extended period of time, allowing for clinically monitoring changes in the tissue at specific sites.

In a preferred embodiment, an absorptivity of a pigment or dye used for forming said visible grid or other type of visible pattern at said tissue-characteristic wavelengths is sufficiently low such that the visible grid or other type of visible pattern is substantially not present in said 2D-PAI images.

According to a further aspect, the above problem is solved by a system for photoacoustic imaging (PAI) and/or ultrasound (US) imaging of biological tissue, in particular a body part, using a PAI probe, said PAI probe comprising a detection device for receiving pressure waves, in particular ultrasonic waves generated upon absorption of said tissue-imaging light pulses, and optionally also ultrasonic waves employed in an additional US imaging mode, and converting said received pressure waves into electrical signals.

Said system further comprises a control device for constructing 2D PAI or US images from said electrical signals, wherein each 2D PAI or US image is associated with a corresponding image plane. Said system further comprises means for providing an optical pattern on or close to the surface of said biological tissue, said optical pattern comprising one or more optical dyes configured for absorbing light at a pattern-characteristic wavelength, wherein said PAI probe is further configured to provide pattern-imaging light pulses having a pattern-characteristic wavelength for which the absorption by said one or more dyes is sufficiently high such that said optical pattern is visible in a 2D PAI image obtained with said PAI probe when employing said pattern-imaging light pulses. Herein, the optical pattern is configured such that the location of the image plane with respect to the optical pattern can be determined at least approximately from said representation of the optical pattern in said 2D PAI image and/or such that the relative location of consecutively taken 2D PAI-images with respect to each other can be at least approximately determined.

The control device is further configured for determining one or both of the location of the image plane of each given 2D PA or US image of said biological tissue with respect to the optical pattern, and the relative location of consecutively taken to de-PAI or US images from the representation of the optical pattern in said given 2D PAI image(s) or in one or more 2D PAI images recorded while the PAI probe is in the same position or a position close to the position in which the given 2D PAI image(s) or US image(s) of said biological tissue is recorded.

In a preferred embodiment, the system comprises at least one light source for providing tissue-imaging light pulses having one or more tissue-characteristic wavelengths to be absorbed in said biological tissue, wherein said system is configured for recording said 2D PAI images of said biological tissue by irradiating, using said at least one light source, tissue-imaging light pulses into said tissue using a PAI probe, said tissue-imaging light pulses having tissue-characteristic wavelengths to be absorbed in said biological tissue, receiving, using said detection device, pressure waves, in particular ultrasonic waves generated upon absorption of said tissue-imaging light pulses in said tissue using said PAI probe and converting said received pressure waves into electrical signals, and constructing, using said control device, 2D images from said electrical signals, said 2D image representing the space-resolved absorption of said tissue imaging-light pulses in a sectional image plane within the tissue.

In a preferred embodiment of the system, said control device is further configured for using said determined location of the image plane of said given 2D PAI/US image for one or more of constructing a 3D image from a plurality of 2D PAI/US images, targeting a specific anatomical location at different points in time, and registering the 2D PAI/US image with imaging data obtained with another imaging modality.

In a preferred embodiment of the system, said optical pattern extends in at least one two-dimensional pattern plane, wherein the control device is configured for determining the location of the image plane of each given 2D PAI/US image of said biological tissue with respect to the optical pattern at least in part by determining a sectional line along which the image plane of said 2D PAI/US image and said at least one pattern plane intersect with each other.

In a preferred embodiment of the system, said PA-probe is configured to be placed on the surface of the biological tissue, in particular the skin of a body part such that the 2D PAI/US image plane is at least approximately perpendicular to the two-dimensional pattern plane.

In a preferred embodiment of the system, said optical pattern has a three-dimensional structure, extending in at least one two-dimensional pattern plane and additionally in a thickness direction perpendicular to said pattern plane, wherein said control device is configured for determining the location of the image plane of each given 2D PAI/US image of said biological tissue with respect to the optical pattern at least in part by determining a sectional plane along which the image plane of said 2D PAI/US image and said three-dimensional pattern structure intersect with each other.

In a preferred embodiment of the system, said optical pattern extends in two or more two-dimensional pattern planes spaced from each other in thickness direction, wherein said control device is configured for determining the location of the image plane of each given 2D PAI/US image of said biological tissue with respect to the optical pattern at least in part by determining a sectional line along which the image plane of said 2D PAI/US image and one of said at least two pattern planes intersect with each other, as well as by determining an angle between said one pattern plane and said image plane of said given 2D PAI/US image of said biological tissue based on at least one other of said at least two pattern planes.

In a preferred embodiment of the system, the optical pattern comprises three or more lines generally extending along, but diverging in an extension direction. Herein, said PAI probe is preferably configured for recording PAI/US images while moving said PAI probe along said extension direction and recording said PAI/US images at different positions along said extension direction.

In a related embodiment, said control device is preferably configured for determining the location of the image plane of each given 2D PAI/US image of said biological tissue with respect to the optical pattern at least in part by determining a position along said extension direction based on distances between representations of said lines, and in particular based on a sum or an average of distances between representations of said lines in said given 2D PAI image, or in one or more 2D PAI images recorded while the PAI probe is in the same position or a position close to the position in which the given 2D PAI/US image of said biological tissue is recorded.

Herein, said control device is preferably further configured for determining an angle between said extension direction and a sectional line of the image plane with a pattern plane in which said three or more lines are arranged, based on distances between presentations of said lines, and in particular based on a difference quotient of distances between representations of said lines in said given 2D PAI image, or in one or more 2D PAI images recorded while the PAI probe is in the same position or a position close to the position in which the given 2D PAI/US image of said biological tissue is recorded.

In a preferred embodiment of the system, said means for providing said optical pattern comprises a foil or a cushion or a pad on which said optical pattern is provided and which is to be placed on top of said biological tissue, in particular on the skin of a body part, wherein in particular, the cushion or pad is preferably partially deformable, and/or is in the form of a collar for placing on a person's neck. Herein, said cushion or pad preferably has a lower side adapted to or capable of adapting to the surface of the biological tissue, in particular the skin at a body part, and an upper side having a flat surface for placing a PAI probe thereon.

In a preferred embodiment of the system, said means for providing said optical pattern comprises a carrier on which said optical pattern is initially provided, wherein said optical pattern is suitable for being transferred from the carrier to a surface of said biological tissue, in particular to the skin of a body part.

In a preferred embodiment of the system, the absorptivity of the of the one or more dyes at the corresponding pattern-characteristic wavelength is a factor of 2 higher, preferably a factor of m higher than at any of said tissue-characteristic wavelengths.

In a preferred embodiment of the system, said at least one light source is configured for providing at least 2, preferably at least 4, and most preferably at least 6 different tissue-characteristic wavelengths.

In a preferred embodiment of the system, the dye is visible in the visible light spectrum, and wherein in particular, said dye is formed by methylene blue or ICG.

In a preferred embodiment of said system, said means for providing said optical pattern is a pen for drawing said optical pattern on the surface of the biological tissue, in particular the skin of a body part, or on a carrier arranged close to said surface of said biological tissue, wherein said control device is preferably further configured for using information derived from a photograph taken of said drawn optical pattern in said step of determining the location of the image plane of each given 2D-PAI or US image of said biological tissue with respect to the optical pattern, and/or in the step of determining the relative location of consecutively taken 2D-PAI or US images.

In a preferred embodiment of the system, said control device is configured for determining the relative location of consecutively taken 2D-PAI or US images employing a continuity constraint on the representation of the optical pattern in said consecutively taken 2D-PAI images, or in 2D-PAI images recorded while a PAI probe is in the same position or a position close to the positions in which the respective consecutive US images of said biological tissue are recorded. In addition or alternatively, the control device may be configured for estimating the speed of a movement of a PAI probe with respect to the biological tissue based on a difference in the representation of the optical pattern in said consecutively taken 2D-PAI images.

In a preferred embodiment of the system, regions within said optical pattern are encoded by one or both of dyes having absorption maxima at different pattern-characteristic wavelengths for different regions within said optical pattern, and by means of a visible grid or other type of visible pattern allowing for identifying regions within said optical pattern by visual inspection.

Herein, the absorptivity of a pigment or dye used for forming said visible grid or other type of visible pattern at said tissue-characteristic wavelengths is preferably sufficiently low such that the visible grid or other type of visible pattern is substantially not present in said 2D-PAI images.

SHORT DESCRIPTION OF THE FIGURES

FIG. 2 is a schematic perspective view of a forearm, a PAI probe and an optical pattern placed in between.

Figure 2:
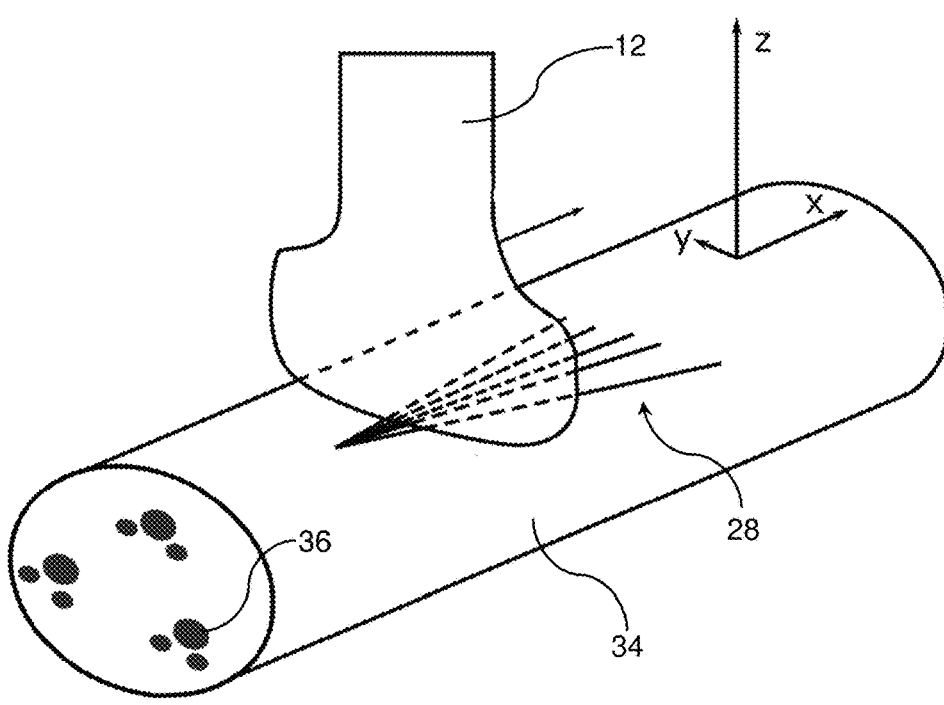
Figure 3:
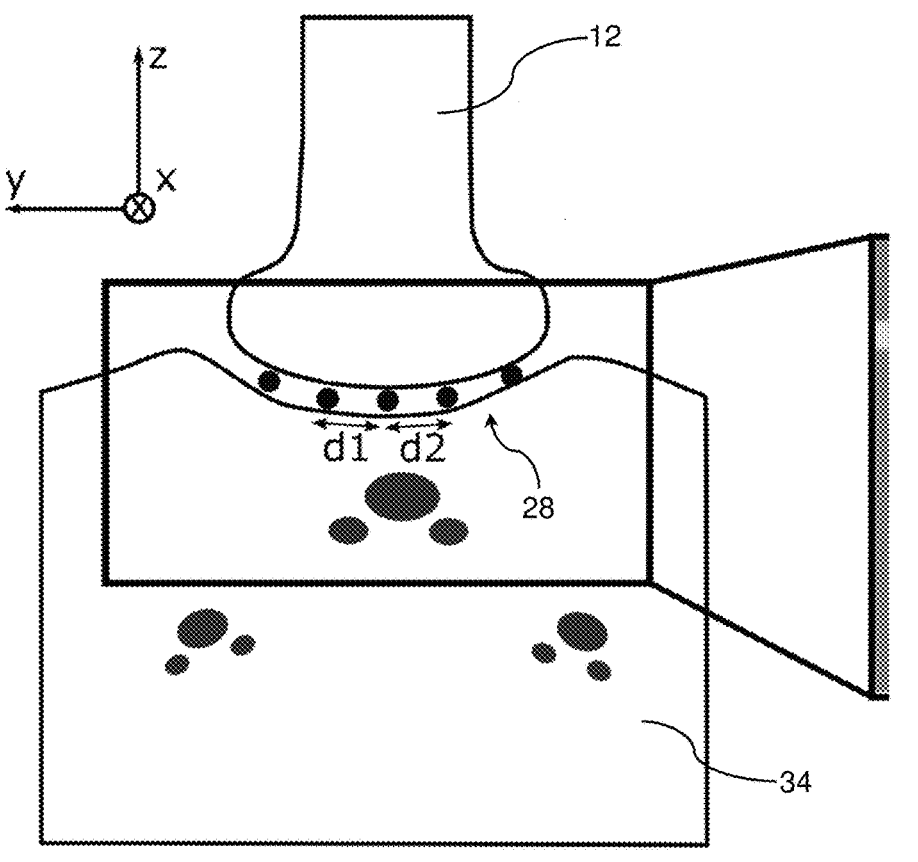
FIG. 3 is a sectional view of the forearm, PAI probe an optical pattern of FIG. 2.
Figures 4, 5:
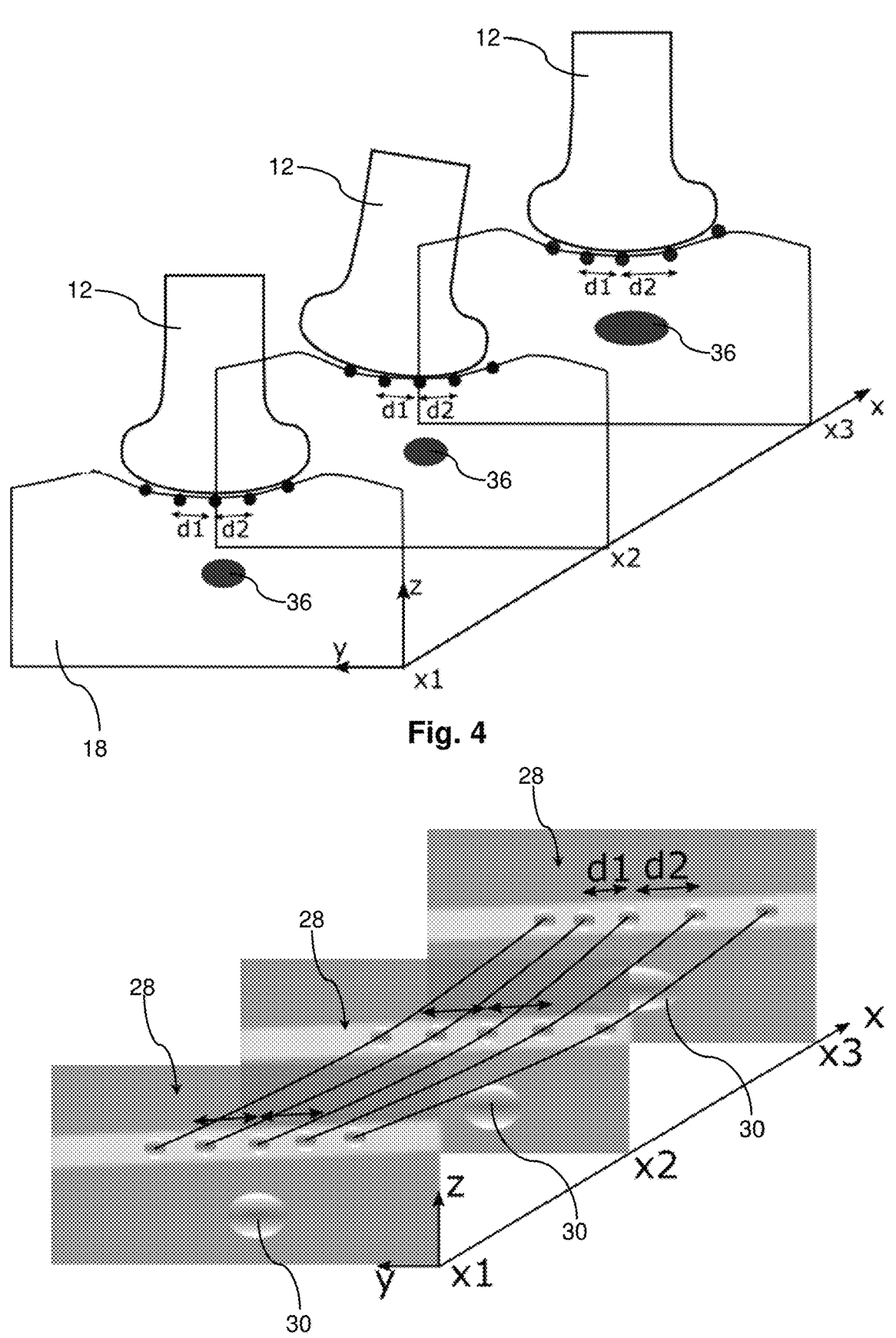

FIG. 4 schematically illustrates three sectional views of snapshots of the PAI probe of FIGS. 2 and 3 moving along the forearm, in three consecutive positions.

FIG. 5 shows schematic representations of three 2D PAI images taken at the three positions represented in FIG. 4, showing both, anatomical structure as well as a representation of the optical pattern.

Figures 6, 7:
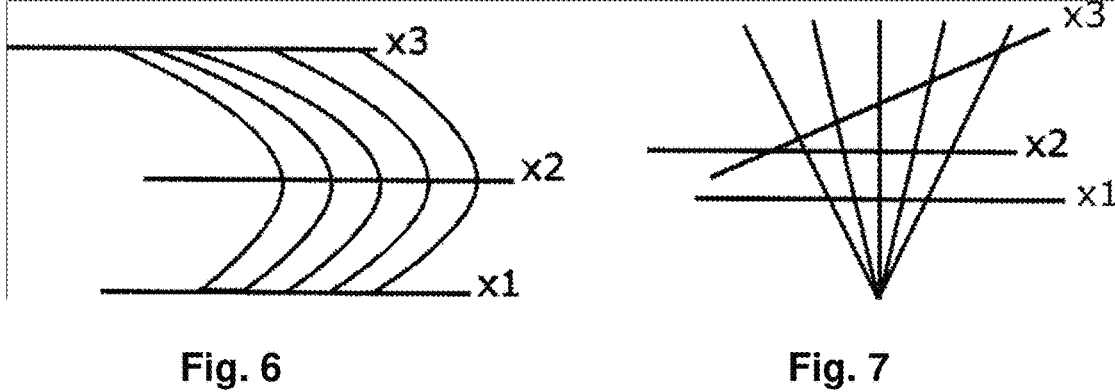

FIG. 6 schematically illustrates the step of analyzing the presentation of the optical pattern within the individual 2D PAI image for determining the location of each 2D PAI image with respect to the optical pattern.

FIG. 7 schematically shows a construction of a 3D image from the individual 2D PAI images based on the determined location of each to de-PAI image with respect to the optical pattern.

Figures 8, 9:
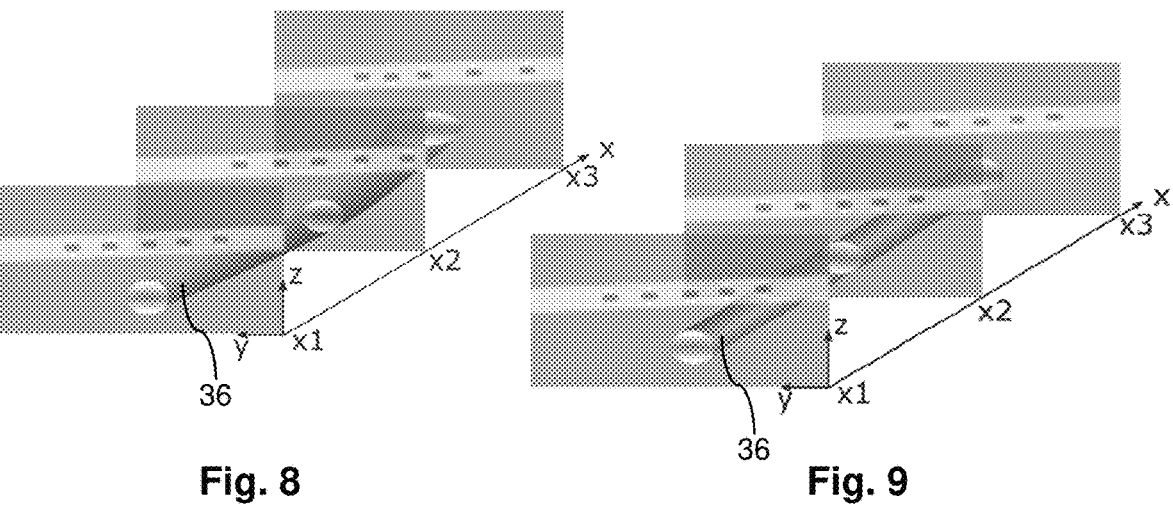

FIG. 8 schematically shows a 3D image reconstructed in a naïve way from the individual 2D PAI images.

FIG. 9 schematically shows a 3D image reconstructed from the individual 2D PAI images based on the determined location with respect to the optical pattern.

Figure 10:
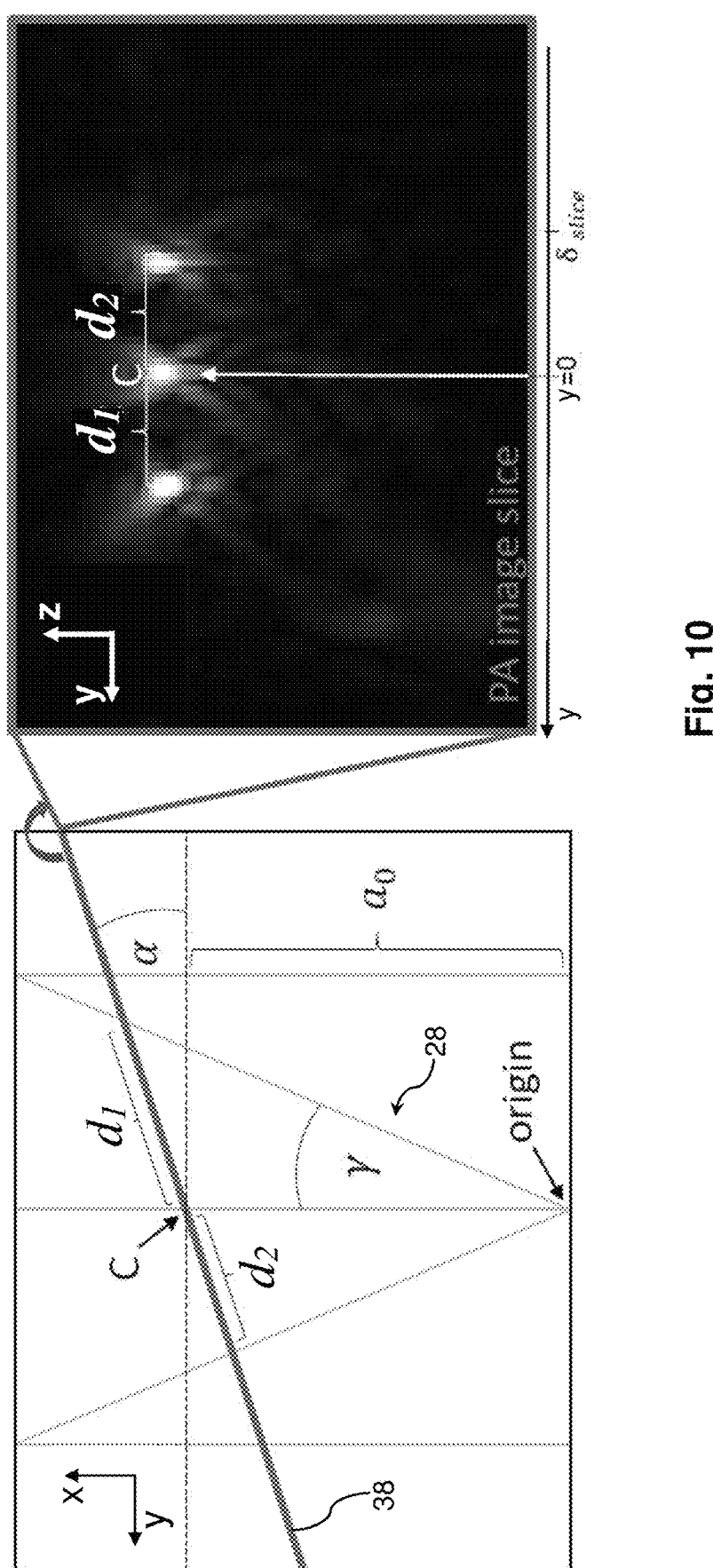

FIG. 10 on the left shows a plan view onto the optical pattern as well as a sectional line along which the 2D image plane and the pattern plane intersect, and on the right the 2D PAI image slice taken in this 2D image plane.

Figure 11:
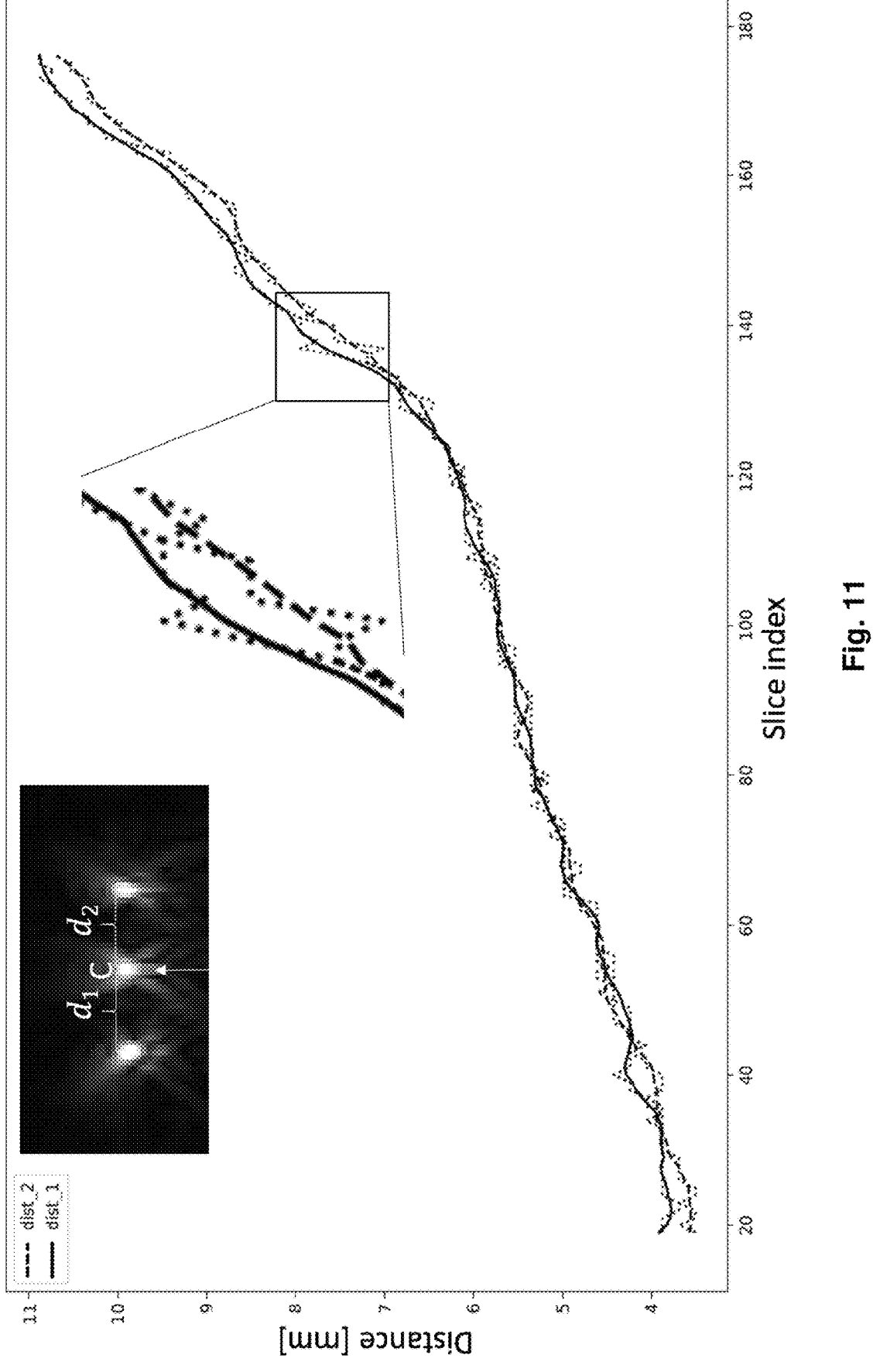

FIG. 11 shows the distances between adjacent lines of the optical pattern in the 2D PAI image plane for a sequence of consecutive 2D PAI images.

FIG. 12 is a schematic perspective view similar to that of FIG. 2, except that a three-dimensional optical pattern is placed between the PAI probe and the skin of the forearm.

FIG. 13 is a perspective view of the three-dimensional optical pattern of FIG. 12.

FIG. 14 is a side view of the three-dimensional optical pattern of FIG. 12.

Figure 15:
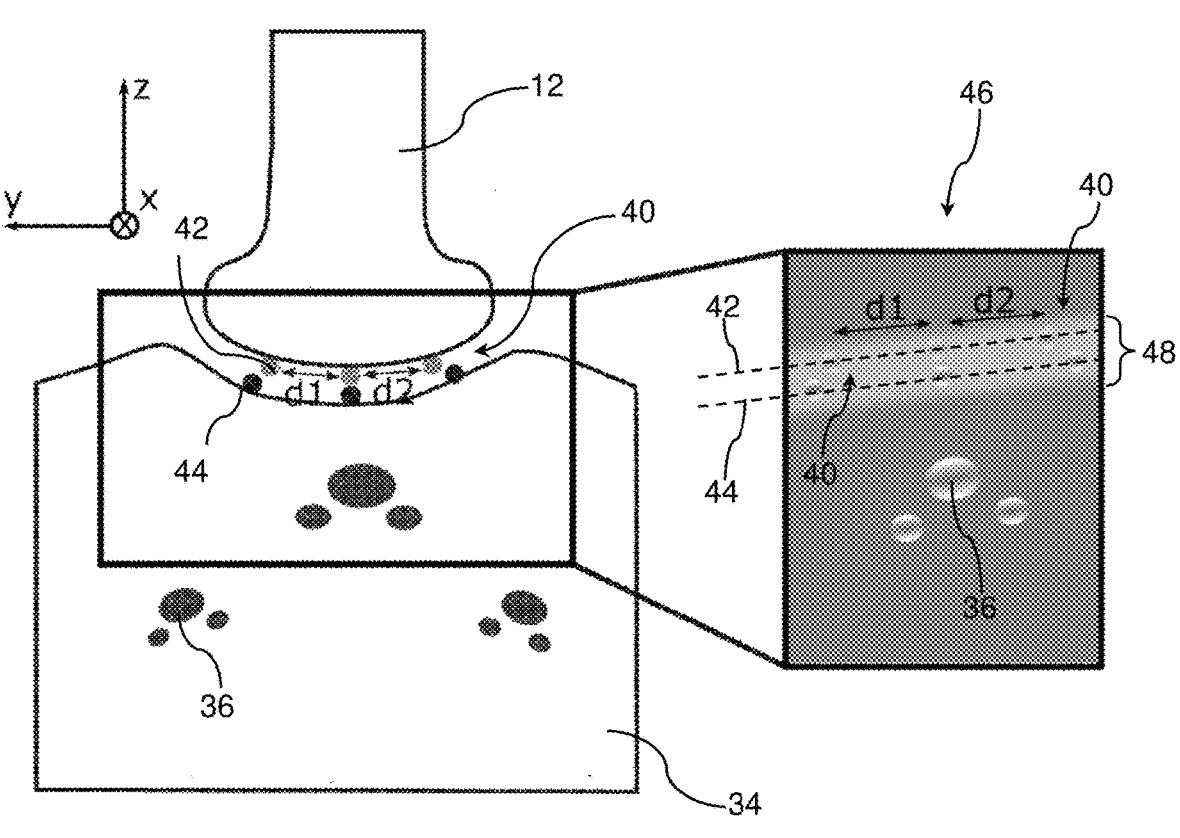

FIG. 15 shows on the left a sectional view of the forearm, the PAI probe and the three-dimensional optical pattern of FIG. 12 in an image claim, and on the right a schematic representation of a corresponding PAI image.

Figure 16:
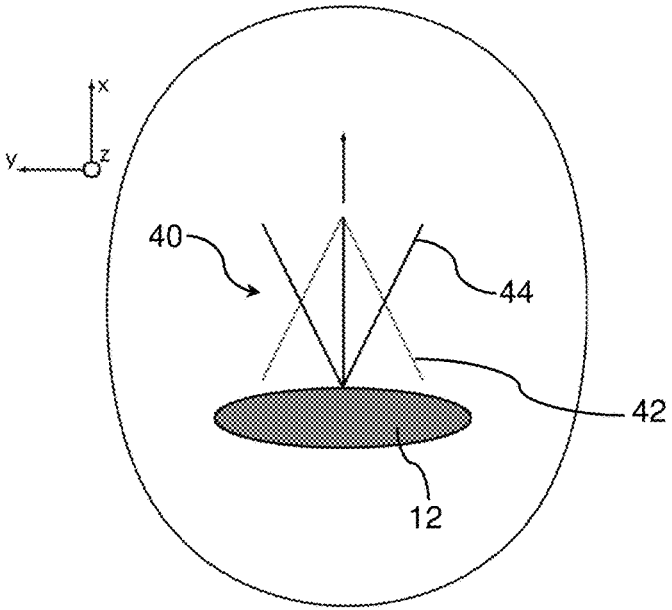

FIG. 16 is a plan view onto the three-dimensional optical pattern and the PAI probe of FIGS. 12 and 15.

FIG. 17 shows 3D images of the optical pattern and blood vessels constructed from 2D PAI images in a naïve way (panels a and b) and using a method according to an embodiment of the invention (panels c and d).

FIG. 18 is a schematic sectional view of a body part, a PAI probe and a gel pad carrying an optical pattern.

FIG. 19 is a schematic view of a person carrying a collar provided with an optical pattern.

FIG. 20 shows a 2D PAI image showing the skin and the optical pattern on the left, and the same image on the right indicating the distance between lines of the optical pattern along the surface of the skin.

FIG. 21 shows a combination of an optical pattern and an MRI contrast agent on a same carrier.

FIG. 22 shows a combination of an optical pattern and a radiopaque marker on a same carrier.

Figure 23:
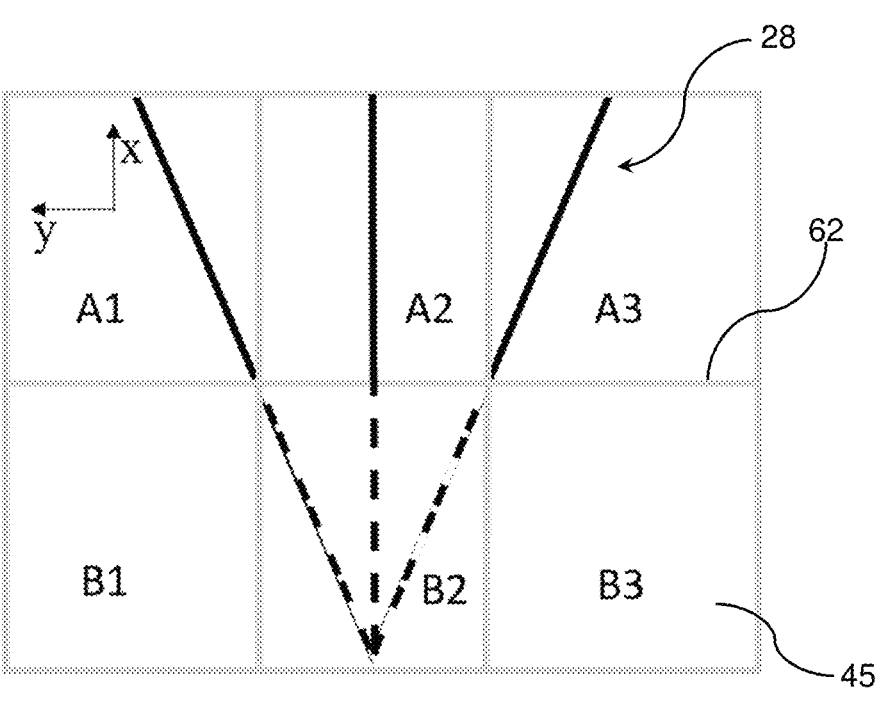

FIG. 23 shows an embodiment of an optical pattern in which different regions are coded by a visible grid and by dyes having different absorption spectra.

Figure 24:
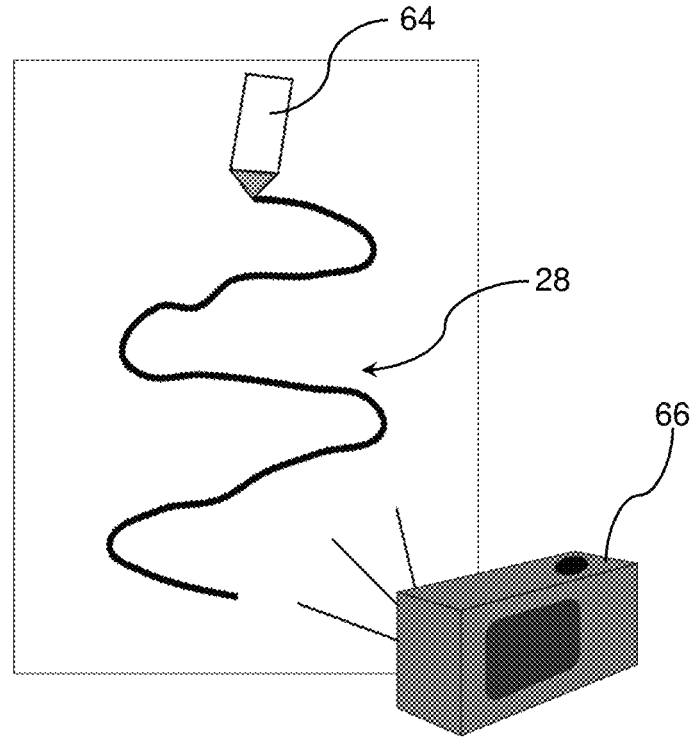

FIG. 24 schematically illustrates an optical pattern which is generated by freehand drawing.

FIG. 25 schematically shows a combination of an optical pattern and fiducial markers provided for other imaging modalities.

FIG. 26 is a photograph of a prototype plastic sheet with an optical pattern printed thereon and removable CT/NMR markers temporarily attached at predetermined locations.

FIG. 27 is a photograph of the top surface of a phantom including target markers.

FIG. 28 shows fused PA and NMR images taken from the phantom of FIG. 27.

Figure 29:
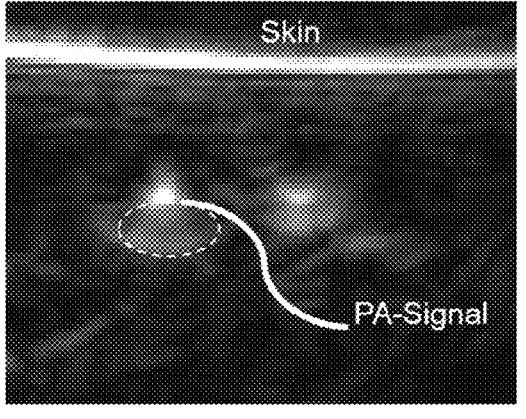

FIG. 29 is a PA image of a body part including a vessel.

Figure 30:
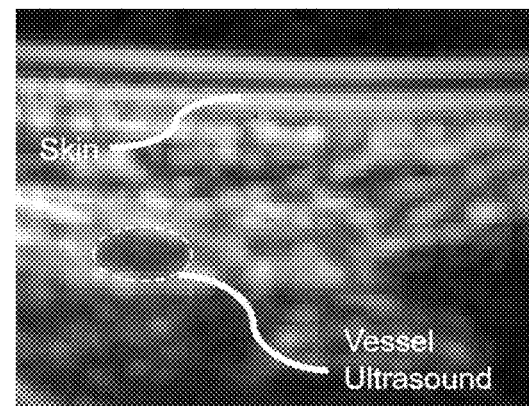

FIG. 30 is a US image of the same volume as in FIG. 29.

Figure 31:
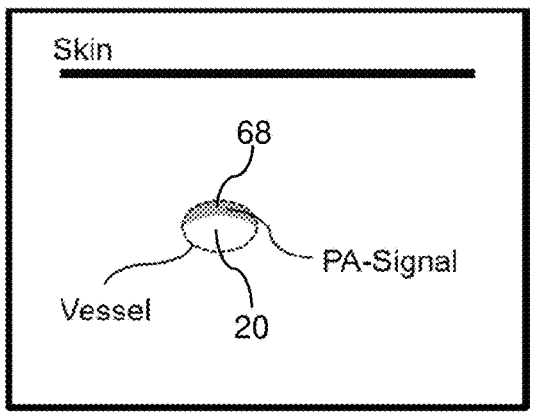

FIG. 31 is a schematic figure explaining the shadowing effect encountered in PAI.

Figure 32:
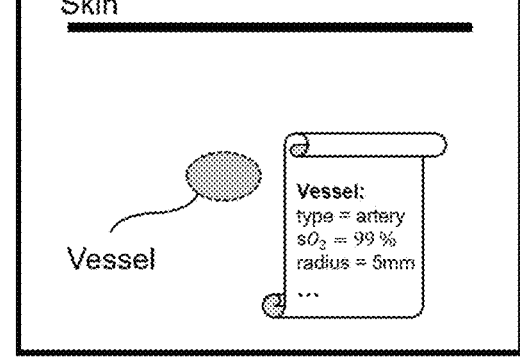

FIG. 32 is a schematic figure illustrating a semantic representation of the PAI volume.

DESCRIPTION OF THE PREFERRED EMBODIMENTS

It is to be understood that both the foregoing general description and the following description are exemplary and explanatory only and are not restrictive of the methods and devices described herein. In this application, the use of the singular may include the plural unless specifically state otherwise. Also, the use of "or" means "and/or" where applicable or unless stated otherwise. Those of ordinary skill in the art will realize that the following description is illustrative only and is not intended to be in any way limiting. Other embodiments will readily suggest themselves to such skilled persons having the benefit of this disclosure. Reference will now be made in detail to various implementations of the example embodiments as illustrated in the accompanying drawings. The same reference signs will be used to the extent possible throughout the drawings and the following description to refer to the same or like items.

Figure 1:
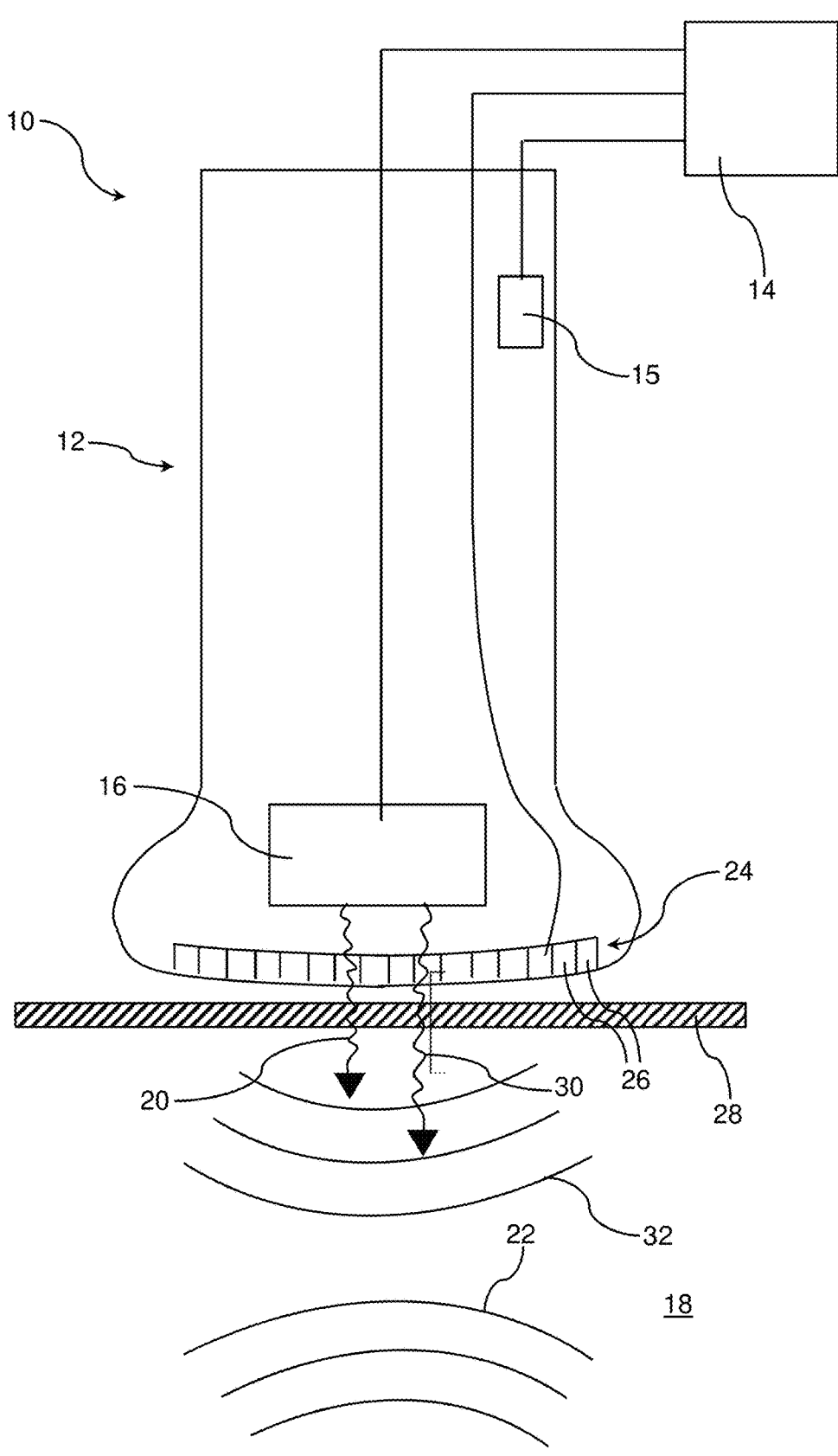
FIG. 1 is a schematic view of a system including a PAI probe, a control device, and an optical pattern.

FIG. 1 is a schematic representation of a system 10 for photoacoustic imaging (PAI) and ultrasound (US) imaging of biological tissue. The system 10 comprises a PAI probe 12 and a control device 14. The PAI probe 12 is a handheld device which allows for both, PAI as well as ultrasound imaging. Preferred embodiments of the present invention allow for both imaging modalities, but at least the PAI modality is required. This is why reference is made to a "PAI probe 12" for short in the following, although it is understood that it may, and in preferred embodiments will, also have ultrasound imaging capabilities.

The PAI probe 12 comprises a light source 16 for photoacoustic imaging. In the embodiment shown, the light source 16 is configured for generating tissue-imaging light pulses of various tissue-characteristic wavelengths to be absorbed in biological tissue 18 under investigation. Light of one exemplary tissue-imaging light pulse is symbolically represented in FIG. 1 under reference sign 20. Some of the light energy radiated into the tissue 18 will be absorbed therein and converted to heat, leading to transient thermoplastic expansion of the tissue 18, which in turn is the source of pressure waves 22, typically in the form of wideband ultrasonic emission. The PAI probe 12 further comprises an ultrasound transducer 24 for receiving and detecting the pressure waves 22. The ultrasound transducer 24 comprises a plurality of transducer elements 26 which in the shown embodiment are formed by piezoelectric elements, and which transform the received pressure wave 22 into electrical signals. The control device 14 is connected to receive these electrical signals and to process the same into a 2D PAI image associated with a corresponding image plane, which is the paper plane in FIG. 1. The control device 14 may comprise one or more microprocessors for carrying out the processing functions described herein under suitable software control. The control device 14 may be a dedicated device reserved for the image processing described herein, or may be formed by a multipurpose computer provided with software to carry out these processing tasks in addition to other tasks. Moreover, the PAI probe 12 comprises an inertial measurement unit (IMU) 15 allowing for measuring a tilt angle of the probe 12.

Note that the magnitude of the ultrasonic emission 22 of the tissue 18, or in other words, the photoacoustic signal, is proportional to the local energy deposition by light absorption. The local energy deposition is a product of absorption and the local fluence, i. e. the light energy per surface area at said location. For a given local fluence value, the photoacoustic signal hence reveals a physiologically specific absorption contrast. As was explained above, this physiologically specific absorption contrast may expose anatomic structures, but is also particularly useful for determining functional tissue parameters, for example blood oxygenation, the distinction of cancerous tissue from non-cancerous tissue or the like. In order to obtain detailed functional tissue parameter information, the light source 16 in the shown embodiment is configured for emitting tissue-imaging light pulses 20 with different tissue-characteristic wavelengths, for example at least four, preferably at least six different tissue-characteristic wavelengths. In the embodiment shown, the light source 16 is a tunable laser source, such that light pulses with arbitrary wavelengths within a predetermined wavelength range can be generated sequentially.

Further shown in FIG. 1 is an optical pattern 28. The optical pattern 28 is provided on top of the biological tissue 18, for example on the skin of a body part. It comprises or is formed by dyes configured for absorbing light at a pattern-characteristic wavelength which is likewise emitted by the light source 16. Accordingly, the optical pattern 28 can be visibly represented in a PAI image recorded with pattern-imaging light pulses, shown at reference sign 30, having said pattern-characteristic wavelength.

The optical pattern 28 is configured such that the location of the image plane of the 2D PAI image with respect to the optical pattern 28 can be determined at least approximately from the representation of the optical pattern 28 in the 2D PAI image recorded with pattern-imaging light pulses. Then, if a 2D PAI image of the tissue is recorded using tissue-imaging light pulses (with a tissue-characteristic wavelength) shortly after or before the 2D PAI image showing the optical pattern, it can be assumed that the PAI probe 12 has not significantly moved in between, and that the location of the image plane obtained for the 2D-PAI image showing the optical pattern is the same as that of the 2D-PAI image showing the tissue. Indeed, it is customary to record the PAI images one wavelength at a time, and to combine the information obtained with different wavelengths sequentially as "one image". In this regard, one may also regard consecutive PAI images recorded with a tissue-characteristic wavelength and a pattern-characteristic wavelength as the same image. This is essentially a question of how the image data is organized. At any rate, when repeatedly recording 2D-PAI images using pattern-imaging light pulses and hence displaying a sectional view of the optical pattern 28, the location of the image plane of the PAI probe 12 with respect to the optical pattern 28 can be determined with sufficient accuracy at all times, and is therefore likewise known for all 2D-PAI images of the tissue 18 taken in between.

The optical pattern 28 may have portions formed by different dyes which can be visualized using different pattern-characteristic wavelengths provided by the light source 16. In preferred embodiments, the dyes are chosen such that they have only little or even negligible absorption for any of the tissue-characteristic wavelengths, such that the optical pattern is "invisible" in the 2D-PAI images representing the tissue 18. For example, the absorptivity of the of the one or more dyes at the corresponding pattern-characteristic wavelength is at least a factor of 2 higher, preferably at least a factor of 10 higher than at any of said tissue-characteristic wavelengths. This way, the quality of the 2D-PAI images of the tissue 18 is not compromised by the optical pattern 28. However, this is not necessary, and in the simplest case, the light source 16 may be configured to emit only a single wavelength, which corresponds to both, the single tissue-characteristic wavelength and the single pattern-characteristic wavelength simultaneously. In other embodiments, there may be plural tissue-characteristic wavelengths, but at least one of them is sufficiently absorbed by the dye of the optical pattern 28 such as to also serve as the pattern-imaging wavelength. In other words, by distinguishing between tissue/pattern-imaging light pulses and tissue/pattern-characteristic wavelengths, it is not meant to suggest that these light pulses or wavelengths must necessarily be different from each other, as long as they are suitable for the respective function.

The PAI probe 12 shown in FIG. 1 is further configured for ultrasound imaging. For ultrasound imaging, the transducer elements 26 are driven to generate an ultrasound pulse symbolically indicated at reference sign 32, and the reflection of this pulse can be recorded by the same transducer elements 26, such that 2D ultrasound images can thereby be recorded. As the skilled person will appreciate, the image plane of such 2D-ultrasound image is the same as the image plane of a 2D-PAI image recorded with the same PAI probe 12 in the same position. Accordingly, the technique described above and in the following for determining the location of an image plane of a 2D-PAI image with respect to the optical pattern 28 can be applied in an analogous manner for determining the location of the ultrasound image plane. It is therefore understood that wherever in the following reference is made to determining the location image planes of the-PAI images, this disclosure likewise applies to ultrasound images without further mention.

With reference to FIGS. 2 to 9, the function of the system 10 of FIG. 1 is explained in more detail. FIG. 2 is a schematic perspective view of a forearm 34, the tissue of which is to be subjected to PAI and possibly also ultrasound imaging. The forearm has only been chosen as a test object for convenience to prove the functioning of the method and apparatus, but it is to be understood that the method can be applied to a large variety of body parts, some of which being explicitly discussed below. On the skin of the forearm, an optical pattern 28 is provided, which in the shown embodiment is formed of five lines which generally extend along an extension erection, which is the x-direction in FIG. 2, but which are diverging in this extension direction. The PAI probe 12 is a handheld device that in operation is to be moved on the body part (in this example forearm 34) along said extension direction (x-direction in the figures), as indicated by the arrow in FIG. 2. Further shown in FIG. 2 are blood vessels 36 that could be the subject of the PAI imaging.

FIG. 3 is a sectional view of the PAI probe 12 and the forearm 34 of FIG. 2. As is seen therein, the lines forming the optical pattern 28 in this sectional view are represented by dots, and this is also the way they will appear in the PAI image. The position of the image plane with respect to the optical pattern 12 can be discerned from the distances d1 and d2 between the central line, which essentially extends along the extension direction (x-direction in the figures), and the two neighboring lines, respectively. Namely, the further the probe 12 moves in x direction, the larger both distances, d1 and d2 in the imaging plane get. Moreover, if the imaging plane is parallel to the y-z plane, the distances d1 and d2 are identical. Any difference between d1 and d2 is indicative of a rotation of the image plane around the z-axis. In other words, from determining d1 and d2, the sectional line between the imaging plane and the plane of the optical pattern 28 can be determined.

FIG. 4 schematically illustrates three sectional views of snapshots of the PAI probe 12 moving in x-direction, in three consecutive positions designated as x1, x2 and x3. FIG. 5 shows schematic representations of three PAI images taken at the positions x1, x2 and x3, each showing representations of the dye pattern 28 as well as of the vessel 36. If the PAI probe 12 was maintaining its pose except for a translation with constant speed in x-direction, a 3D image could be constructed from the sequence of individual 2D image slices in a straightforward manner, by stacking the 2D image slices in x-direction at a distance corresponding to the product of the translation speed and the image acquisition rate. This is referred to as the "naïve construction" herein. However, in a handheld device, the actual motion will deviate from this idealistic behavior. For example, the probe 12 may deviate from this idealistic behavior by a shift in the y-z plane, as seen in FIG. 5 from the fact that the lines forming the optical pattern 28 in the naïve construction of the 3D image are no longer straight, and as is also indicated in FIG. 6. Such a shift in y-z plane, however, can be rather easily compensated since the lines of the pattern 28 are represented in each of the PAI images, so that the location of the image within the x-z plane can be readily determined. The same is true for a possible tilt of the probe 12 in the y-z plane, which can likewise be readily compensated based on the representation of the lines of the pattern 28 in the PAI image.

A further deviation from the idealistic translation is a rotation of the 2D-PAI image plane around the z-axis, which leads to a difference in the distances d1 and d2 from each other, that can likewise be seen in FIG. 6. With reference to FIG. 10, it is explained how the corresponding rotation angle α of the image plane with respect to the y-z plane can be derived from the distances d1 and d2.

FIG. 10 shows on the left a top view onto the optical pattern 28, which in this case includes only three diverging lines, and which defines a reference coordinate system. In this embodiment, it is assumed that the optical pattern 28 is flat and is arranged in the x-y plane. The line in the middle (centerline of the following) extends in the x-direction. The two adjacent lines to both sides likewise generally extend in the x-direction, but diverge from the centerline/x-axis by an angle γ. The point where the three lines cross is the origin of the coordinate system defined by the optical pattern 28.

The image plane is shown at reference sign 38 in FIG. 10. The PAI image of the respective 2D-PAI image slice is shown in the right part of FIG. 10. The three bright spots shown therein correspond to the representation of section of the three lines forming the optical pattern 28 with the 2D-PAI image plane 38. As apparent from the left part of FIG. 10, the rotation angle α of the 2D-PAI image plane 38 with respect to the y-z plane can be determined from the distances d1 and d2 between the intersections of the lines of the optical pattern 28 with the 2D-PAI image plane 38 as follows:

$$\alpha = \frac{1}{\tan(\gamma)} \cdot \frac{d1 - d2}{d1 + d2}$$

The x-coordinate of the intersection of the 2D-PAI image plane 38 with the centerline of the pattern 28, referred to as a0 in the following, can be calculated from d1 and the angles α, γ as follows:

$$a0 = \frac{d1}{\tan(\gamma)}\left[\frac{\tan(\alpha)}{\tan\left(\frac{\pi}{2} - \gamma\right)} + \cos\alpha\right]$$

Note that the angle α and the distance a0 from the origin define the sectional line along which the image plane 38 of the PAI image and the plane of the optical pattern 28 intersect with each other. With this sectional line, and a straightforward correction for translations and rotations of the probe 12 within the y-z plane, all degrees of freedom of the probe 12 are accounted for, except for a possible tilt of the PAI probe 12 in the x-z plane. It is however seen that in practice, this possible tilt does not necessarily have to be accounted for, since it is actually possible to avoid such a tilt quite reliably in handheld operation. In other words, when the operator tries to keep the probe 12 perpendicular to the plane of the optical pattern 28, it can simply be assumed that the 2D-PAI image plane 38 is perpendicular to the plane of the optical pattern 28 (referred to as the "at least one pattern plane" in the summary above). Possible ways for correcting for this tilt where needed or desired will be described below.

It is hence seen that for every pixel in the 2D-PAI image plane that is spaced by a distance $\delta_{slice}$ from the line where y=0, the coordinates within the reference coordinate system defined by the optical pattern 28 can be determined as follows:

$$y = -\cos(\alpha) \cdot \delta_{slice}$$

$$x = \sin(\alpha) \cdot \delta_{slice} + a_0$$

FIG. 11 shows the distances d1 and d2 recorded for 180 consecutive 2D-PAI images or "slices". The measured individual values of d1 and d2 are shown by dotted lines and are found to be somewhat noisy, which is why smoothened curves are presented, which give a realistic representation of the distances d1 (solid lines) and d2 (broken lines). From these smoothened curves, the sectional line along which the image plane 38 of said 2D-PAI image and the pattern plane intersect with each other can be determined, as represented by the parameters a0 and α. These sectional lines as determined for the situation in FIG. 6 are schematically shown in FIG. 7, where the respective image planes and the images therein are aligned with the coordinate system defined by the optical pattern 28.

Note that if the probe 12 was held perfectly orthogonal to the optical pattern 28, with an angle α=0, and was merely translated at constant speed in x-direction, the curves for d1 and d2 seen in FIG. 11 should be identical and should be a linear graph. While the operator tried to move the hand-held probe 12 in this manner, it is seen that the translation speed increased during the second half of the operation and that the distances d1 and d2 are at each time similar, but not perfectly identical, giving rise to a non-zero rotation angle α.

FIG. 8 schematically shows a sequence of 3 2D-PA images in such handheld operation. Due to the deviation from the idealized constant speed translation in x-direction, a 3D image constructed in a naïve manner from consecutive image slices would not represent the correct anatomy. However, by accounting for the location of each 2D-PAI image plane with respect to the optical pattern 28, as well as for the position of the image arranged within this 2D-PA image plane, a realistic 3D image can be constructed, as shown in FIG. 9.

In the embodiment shown in FIGS. 2 to 11, the optical pattern 28 extends only in a single two dimensional pattern plane, where the diameter of the individual lines is negligible for all practical purposes. Accordingly, the pattern plane and the 2D-PAI image plane only intersect along a line. However, in other embodiments, said optical pattern may have a three-dimensional structure, extending in at least one two-dimensional pattern plane and additionally in a thickness direction perpendicular to said pattern plane. In this case, the intersection between the 2D-PAI image plane and the three-dimensional optical pattern is a section plane rather than a section line, which section plane is represented in the 2D-PAI image. Based on this representation, again the location of the 2D-PAI image plane with respect to the optical pattern can be determined. In particular, other than in case of a purely two-dimensional optical pattern, in this case also the angle under which the 2D-PA image plane and the optical pattern intersect with each other, can be determined from the representation of the three-dimensional optical pattern in the 2D-PAI image.

An example for a three-dimensional optical pattern 40 is shown in FIGS. 12 to 16. FIG. 12 is a schematic perspective view similar to that of FIG. 2, except that a three-dimensional optical pattern 40 is placed between the PAI probe 12 and the skin of the forearm 34. FIGS. 13 and 14 show a perspective view and a side view of the three-dimensional optical pattern 40, respectively. The three-dimensional optical pattern 40 extends in two two-dimensional pattern planes 42, 44 spaced from each other in a thickness direction, as best seen in FIG. 14. Each of the pattern planes 42, 44 includes three diverging lines similar to the optical pattern 28 shown in the previous embodiment, wherein, however, the lines in the upper pattern plane 42 converge in positive x-direction while the lines in the lower pattern plane 44 diverge in positive x-direction. In the shown embodiment, the portions of the pattern in the pattern planes 42, 44 are formed from a different dye, and the light source 16 is configured for emitting pattern-imaging light pulses of two corresponding pattern-characteristic wavelengths matching the absorption peaks of the dyes. While it would be possible to form the two pattern planes 42, 44 with the same dye, this way the imaging of the individual pattern planes 42, 44 will be improved. The dyes are embedded in a foil 45 made from plastic that can be placed between the skin of the forearm 34 or any other object to be subjected to imaging and the PAI probe 12. The foil 45 allows for coupling the pressure waves between the tissue 18 of the forearm 34 and the PAI probe 12. For improved acoustic coupling, a thin film of gel (not shown) as commonly used in ultrasound imaging can be placed between the skin and the three-dimensional optical pattern 40 as well as between the three-dimensional optical pattern 40 and the PAI probe 12.

FIG. 15 is a sectional view of the forearm 34, the PAI probe 12 and the three-dimensional optical pattern 40 placed in between, where only the dye portion of the optical pattern 40 is shown, but not any matrix material such as the plastic foil 45 in which the dye is embedded. FIG. 16 is a corresponding plan view. Further shown in FIG. 15 on the right is a schematic representation of the actual PAI image 46 recorded in this configuration. Note that this PAI image includes both, anatomical/tissue related information, such as a representation of a vessel 36, as well as a representation of the three-dimensional optical pattern 40. It is understood that these parts of the image are recorded sequentially using tissue-imaging light pulses at one or more tissue-characteristic wavelengths, as well as pattern-imaging light pulses at two different pattern-characteristic wavelengths. The imaging itself is carried out one wavelength at a time, but the results can be combined in a common 2D-PAI image 46 as shown in FIG. 15. For simplicity, the actual object (vessel 36, optical pattern 40) as well as the representation in the two-PAI image 46 are designated with the same reference signs.

As is seen in the schematic representation of the 2D-PAI image 46, the intersection between the 2D-PAI image plane 38 (paper plane in FIG. 15) and the three-dimensional optical pattern 40 is in this case a section plane 48 rather than a section line, and this section plane 48 is represented in the 2D-PAI image. As before, from the distances between adjacent lines in each pattern plane 42, 44, the position of the 2D-PAI image plane along the x-axis (extension direction), i.e. the parameter a0, as well as the angle α between the 2D-image plane and the y-z can be determined in the same manner as described above. However, from the distances between the lines in the individual pattern planes 42, 44, also the aforementioned tilt of the PAI probe 12 in the x-z plane can be determined. For example, in this embodiment, the step of determining the location of the image plane 38 of the 2D-PAI image 46 image of the tissue with respect to the optical pattern 40 may comprise determining a sectional line along which the image plane 38 of said 2D-PAI image 46 and one of said at least two pattern planes, for example the upper image plane 42 intersect with each other, as well as a step of determining an angle between the upper pattern plane

42 and said image plane 38 of said given 2D-PAI image of the tissue based on the lower pattern plane 44. For example, the parameter a0 can be individually determined based on both pattern planes 42, 44, and tilt angle can be calculated by trigonometric relations based on the difference in the two values for the parameter a0 and the distance between the pattern planes 42, 44.

While the three-dimensional optical pattern 40 hence allows for an even more precise determination of the location of the 2D-image 46 with respect to the optical pattern 40, this comes at the price of a loss in available imaging depth corresponding to the thickness of the three-dimensional optical pattern 40. It hence depends on the specific application whether it is more advantageous to make use of a three-dimensional optical pattern such as the pattern 40 or a two-dimensional optical pattern such as the one shown at reference sign 28 above. As mentioned before, even when using a purely two-dimensional optical pattern, which would not allow to assess the tilt angle between the pattern plane and the image plane, good results can be obtained, as is demonstrated with reference to FIG. 17 next.

FIG. 17 shows in panels a and b 3D images constructed in the naïve manner from individual 2D-PAI based on the assumption that the probe is properly positioned and translated with constant speed along the x-axis only. The constructed 3D image shows both, the representations of the (two-dimensional) optical pattern 28 and of the vessels 34 in different colors, but in the black and white representation of FIG. 17, the parts of the 3D image corresponding to the optical pattern 28 and the vessels 34 are shown separately in panels a and b, respectively. It is seen in panel a that the representation of the optical pattern 28 deviates from the true optical pattern 28, indicating that the 3D image thus constructed is not precise. This is also confirmed from the representation of the vessel structure 34 which obviously fails to deliver the true anatomy.

Panels c and d show 3D images constructed from the same 2D-PAI images, but accounting for the location of each 2D-PAI image with respect to the optical pattern 28. As is seen from panel c, in the properly constructed 3D image, the representation of the optical pattern 28 is close to the true geometry thereof. Moreover, the vessel structure 34 is represented much more realistically in the 3D image. Note that these images were recorded with a two-dimensional optical pattern 28 only, and without correcting for the angle between the pattern plane and image plane, relying on a proper pose in this regard during the freehand operation.

Errors due to a possible tilt of the PAI probe 12 in the x-z plane may also be avoided by other means than a three-dimensional optical pattern, such as the above pattern 40. For example, the tilt angle may be measured using the inertial measurement unit (IMU) 15 shown in FIG. 1. Note that one of the attractive features of the present invention is that it in principle does not need any additional navigation means for estimating the pose of the PAI-probe 12, but merely relies on the optical pattern 28, 40 and its representation in the PAI-images. Accordingly, providing the IMU 15 could look like a deviation from this attractive concept. However, while additional navigation apparatus for full pose estimation would usually increase the equipment cost, complexity and bulkiness significantly, the IMU 15 is a comparatively simple and cheap device that can be used to augment the pose determination with respect to only one degree of freedom of the pose estimation in the present invention, which still to the most part is based on the optical pattern.

Another way of estimating the tilt angle may be based on a change of reflectivity of the surface of the optical pattern 28, or of a foil on which, or a matrix in which it is provided, using the Fresnel equations. In the alternative, if e.g. the absorption coefficient of the dye of the centerline and the pulse energy of the light source 16 is known, an expected PAI signal amplitude can be calculated. This expected amplitude can be compared to the measured amplitude, enabling the estimation of the tilt angle. The rationale of this is that the amplitude of the measured signal is expected to decrease with an increased tilt of the PAI probe 12.

The optical pattern 28, 40 can be provided in different ways. In some embodiments, it will be printed on a foil or embedded in a matrix. In other embodiments, it may be attached directly to the surface of the biological tissue, such as the skin of a body part, for example in a similar manner as a "fake tattoo" is attached to skin. The precise structure of the optical pattern 28, 40 and its carrier, if any, can be chosen depending on the anatomy of the target tissue.

In the trunk area, the pattern 28, 40 could e.g. be used for diagnosing Crohn's disease, for mamography and general angiography/cardiovascular diseases, such as monitoring of the vessels, calcification of the vessels, diagnosing thrombosis et cetera. Since in these regions the tissue is comparatively soft, a simple pattern provided on a plastic foil to be placed on or attached to the skin will often be sufficient.

In the head and neck area, various structures, including lymph nodes, thyroid, parotid gland, other muscles and glandular tissue may be displayed in PAI images (and alternatively or additionally, ultrasound images) together with the optical pattern 28, 40. These are particularly important objects for PAI images in the context of diagnosis and therapy of tumors, but also, for example, for the analysis of malfunctions or anomalies. For this purpose, the optical pattern 28, 40 could be provided on a partially deformable gel pad 50 as shown in FIG. 18 to compensate for anatomical irregularities. Note that the gel pad 50 shown in FIG. 18 has a flat upper surface 52 for placing the PAI probe 12 thereon. the upper surface 52 assists in placing and maintaining the PAI probe 12 perpendicular to the optical pattern 28, and hence is an example of the aforementioned guiding means. The gel pad 50 further has a lower surface 54 at which the pad 50 is deformable and can conform to the body part. Such gel pad 50 can for example also be devised for placing to the heel area of a patient for collagen measurement in muscular dystrophy patients.

FIG. 19 shows a pad 56 on which the optical pattern 28 is provided, which is shaped like a collar that can be placed around a person's neck.

Note that in many applications, the optical pattern 28, 40 may be fixed on the skin beyond the period of the pure measurement, for example for a full cycle of planning, therapy process and after-care. This is particularly useful for tumor aftercare and tumor response. Further useful applications are the field of thermal coordination for ablations, for example in the thyroid gland.

While in preferred embodiments, the optical pattern 28 is a two-dimensional object, defined by a pattern plane, this pattern plane need not be flat. Indeed, it is seen that in many cases the pattern will conform to the skin of the body part under investigation, which will often be curved. Still, even in the curved state, when adapted to the surface of the skin, the optical pattern 28 may serve as a reference for the 2D-PAI images. Namely, the local curvature of the pattern can 28 be determined from the PAI images 46 and hence accounted for. The left part of FIG. 20 shows a 2D-PAI image in which the section of three lines of the optical pattern 28 are shown, together with the skin on which the pattern 28 is provided. Namely, due to its prominent absorption characteristic, the skin can be visualized in the PAI image. One can therefore perform a segmentation based on signal intensities and calculate the path length of the skin between the lines of three absorption peaks, corresponding to the lines of the optical pattern 28. This or similar methods may be used for correcting for deformations in a manner per se known to the skilled person.

A further important use of the optical pattern 20, 40 is to provide a calibration standard for quantitative photoacoustic imaging. Quantitative photoacoustic imaging herein means that some sort of quantitative measure of the absorptivity of the tissue is determined. This is particularly important for functional imaging, such as oxygenation or the like. Currently, it is also difficult to compare PAI images recorded with different apparatuses, because signal intensities obtained for the same tissue with different apparatuses will usually differ from each other. Using the optical pattern having a known absorptivity, the signal intensity in the PAI image can be calibrated or normalized.

A yet further important use of the optical pattern 28, 40 is for the purpose of co-registering the PAI-images or ultrasound images with images recorded with other imaging modalities, such as MRI, multispectral imaging or CT. In some embodiments, the dye used in the optical pattern may be also "visible" in the other imaging modality. In the alternative, a further contrast pattern may be provided that can be discerned in the additional imaging modality and that is provided in a fixed spatial relationship to the optical pattern 28, 40. Two examples are shown in FIGS. 21 and 22, respectively.

FIG. 21 shows an optical pattern 28 of the type described with reference to FIGS. 2 to 11, which is provided on a transparent plastic foil 45. On the same plastic foil 45, MRI contrast agents 58 are provided, which may for example be formed by or include gadolinium.

FIG. 22 shows again an optical pattern 28 of the type described with reference to FIGS. 2 to 11, which is provided on a transparent plastic foil 45. On the same plastic foil 45, in this case radiopaque markers 60 are provided, which are formed by a pair of diverging lines. Using the combined patterns of FIG. 21 or FIG. 22, the patent coordinate system can be decoded with both imaging modalities, allowing for multimodal image registration.

FIG. 23 shows a further embodiment of an optical pattern 28 provided on a carrier 45. The carrier 45, and also the optical pattern 28 are divided in six areas, arranged in two rows and three columns. These areas are marked by a visible grid 62, allowing to identify the six regions by visual inspection. In the embodiment shown, the grid 62 is formed by dyes or pigments that are visible in the visible spectrum of light, but which are "invisible" in the PAI imaging of the tissue and the pattern 28. In other words, the dye or pigment forming the grid 62 has only very little absorption at any of the tissue-characteristic or pattern-characteristic wavelengths. This way it is ensured that the grid 62 does not interfere with the PAI imaging.

Moreover, in the embodiment of FIG. 23, the optical pattern 28 has different regions having absorption maxima at different pattern-characteristic wavelengths. The portion of the optical pattern 28 in the first row includes dyes having a different absorption characteristic than the dyes in the portion of the optical pattern 28 in the second row, which is illustrated in FIG. 23 by solid and broken lines, respectively. In other words, the different regions of the pattern have a different "color" in the PAI imaging. This means that from any PAI image, it can immediately be seen in which of the regions it was recorded, which is very helpful for the person interpreting the individual PAI images.

Moreover, the grid will assist the user in re-examining a position where a PAI image has previously been taken. As is seen from FIG. 23, the the grid 62 represents a coordinate system similar to that in a geographic map. When establishing the position of a 2D-PAI image with respect to the optical pattern 28, the coordinates with respect to the visible grid can be likewise established. These coordinates may be stored together with the 2D-PAI images. Then, if the user wishes to revisit a location where a PAI image has been previously taken, the specific location can be readily found based on the coordinates and by visual inspection of the grid 62.

As the skilled person will appreciate, the example shown in FIG. 23 represents a fairly simple embodiment for illustration purposes. In other embodiments, the grid 62 may have a considerably higher resolution, and there could be more than two regions encoded by different dyes of the optical pattern 28.

In the embodiment of FIG. 23, the carrier 45 is suitable to remain on the skin of a body part for an extended time. This allows for constantly revisiting specific locations and monitoring clinical changes, such as healing processes, tumor growth or the like.

In the embodiments described above, the optical pattern 28 was always designed such that it permits determining the location of an image plane with respect to the optical pattern 28, which in particular required that the precise geometry of the optical pattern 28 was known, including e. g. a possible deformation of the optical pattern. However, in other embodiments, the optical pattern is used for determining the relative location of consecutively taken 2D-PAI images with respect to each other, at least approximately. This can for example be done using a continuity constraint on the representation of the optical pattern in consecutive 2D-PAI images. For this, it is sufficient if the pattern 28 consists of or at least comprises a number of continuous objects, such as continuous lines. The continuity constraint means that the relative locations of the consecutively taken 2D PAI images should be such that the continuity of these continuous objects is preserved. This can be used as a constraint in an algorithm that determines the relative location of the consecutive 2D-PAI images.

As the skilled person will appreciate, for this purpose, a large variety of patterns can be used, and the geometry of the patterns need not even be known. In a simple but very useful embodiment discussed with reference to FIG. 24, the optical pattern 28 may simply be drawn freehandedly on the skin of the body part using a pen 64. The pen 64 utilizes an ink containing dyes that may be of the type discussed above with reference to the prefabricated optical patterns 28. Instead of drawing the pattern 28 directly on the skin, it is also possible to draw it on a carrier arranged close to the surface of the skin, such as a film or foil provided on the skin. Such a freehand optical pattern 28 may be used for determining the relative location of consecutively taken 2D-PAI images, e.g. using said continuity constraint on the representation of the optical pattern in consecutive 2D-PAI images. For this purpose, continuous, curvy lines, possibly including loops as drawn by freehand using a pen 64 are very well suitable.

Moreover, the speed of a movement of the a PAI probe 12 with respect to the biological tissue during the imaging process may be assessed based on a difference in the representation of the optical pattern 28 in consecutively taken 2D-PAI images. Namely, for any pattern structure that is not parallel to the direction of the movement of the PAI probe, and in particular for a freehand pattern portions having curvy lines and loops, the deviation between the representations of the pattern structure in consecutively taken 2D-PAI images increases with the speed of the probe 12. The assessment of this speed can be used for various purposes, for example for assisting the user in carrying out the scan with an approximately constant speed, or for estimating the distance between consecutively taken 2D-PAI images, which is proportional to the speed.

Note that for both, determining the speed of the probe 12 or the relative location of consecutive PAI images by the continuity constraint, it is not necessary that the precise shape of the pattern 28 is known, as these assessments rely on the comparison of the representation of the optical pattern 28 in consecutive 2D-PAI images rather than with a known geometry of the optical pattern 28. However, in a preferred embodiment, a photograph of the drawn optical pattern may be taken using the camera 64. Then, information derived from said photograph may be used in determining the location of the image plane of each given 2D-PAI or US image of said biological tissue with respect to the optical pattern, and/or in the step of determining the relative location of consecutively taken 2D-PAI or US images.

FIG. 25 schematically shows an optical pattern 28 together with four fiducial markers 58 for NMR imaging in a predetermined spatial relationship. These fiducial markers 58 are examples of the aforementioned "additional contrast agents". As mentioned before, in some embodiments it is possible to permanently provide the optical pattern 28 and the fiducial markers 58 on a same carrier, such as a plastic foil as shown under reference sign 45 in FIGS. 21 and 22. However, in preferred embodiments, the fiducial markers 58 are configured to be only temporarily provided on the same carrier, typically only for the time of recording images with said other imaging modality.

FIG. 26 shows a photograph of a prototype plastic foil 45 on which an optical pattern 28 of the type described above is provided. Also shown are fiducial markers 58, each comprising a liquid contrast agent encapsulated in a corresponding plastic sphere. As was mentioned above, the fiducial markers 58 containing the contrast agent may be generally referred to pars pro toto as "contrast agent" herein. The fiducial markers 58 are placed at distinct positions which are marked by ink printed on the plastic foil 45, wherein said ink is not (or only little) absorbing at any of the pattern-characteristic or tissue-characteristic wavelengths used in the PAI imaging.

In an exemplary workflow, first the plastic foil 45 having the optical pattern 28 printed thereon, but without the fiducial markers 58 attached thereto, is attached to the skin of a patient, and a photoacoustic scan is performed. Afterwards the fiducial MR/CT markers 58 ("i.e. contrast agents") are attached on said distinct positions on the plastic foil 45, which is still attached to the patient's skin. A NMR or CT scan is performed. Since the position of the fiducial markers 58 relative to the optical pattern 28 is known, an accurate point registration between the PAI image and the NMR or CT image is easily possible. The fiducial markers 58 generate a bright signal in the NMR or CT image, respectively. The NMR or CT fiducial markers 58 can then be easily removed from the plastic foil 45, allowing to perform further photoacoustic scans also after the NMR/CT scan.

Indeed, in preferred embodiments, as was explained above, a plurality of sets of PAI images taken at different points in time may be co-registered with the same image recorded with another imaging modality such as CT or NMR imaging. In a preferred workflow, a CT or NMR image of the region of interest is recorded only once at the beginning of an extended treatment or monitoring period. The CT image or NMR image is preferably used for obtaining anatomical or morphological information at very high resolution throughout the volume of interest. In the course of the treatment or monitoring, various sets of PAI images can then be recorded at different times, for example to monitor functional parameters over time, such as oxygenation, flow direction of blood or the like. Due to the spectroscopic character of the PAI method, it is well suitable for assessing information on a molecular level. For visualizing the anatomy of the body part, however, other imaging modalities like CT or NMR will usually be superior. Since the anatomy will not change over the course of the treatment or monitoring period, it is sufficient to record one CT or NMR image at the beginning of the treatment/monitoring period, and combine the anatomical information derived therefrom with the functional information obtained easily and cheaply as needed by PAI imaging. According to this workflow, the optical pattern 28 would remain attached to the patient for the duration of the treatment or monitoring period. Obviously, even if the CT or NMR fiducial markers 58 were designed in a way that they would allow for recording PAI images, it is more practical and comfortable to remove them from the carrier, such as the plastic foil 45, once they are no longer needed. Moreover, the removed fiducial markers 58 may be reused for another application at the same patient or even a different patient. Since in the shown example they are only in contact with the plastic foil 45, they do not need to be absolutely sterile and can therefore be in principle cleaned and used again.

The prototype plastic foil 45 including the optical pattern 28 and the removable fiducial CT/NMR markers 58 as shown in the photograph of FIG. 26 were used together with a phantom shown in the photograph of FIG. 27. In the phantom, three groups of three target markers 66 each were molded into an agar phantom body in three layers at different distances from the surface. The photograph of FIG. 27 shows a top view, where the three target markers 66 in the layer closest to the surface can be clearly seen, while the target markers 66 in the next closest layer are already blurry and the target markers 66 in the layer furthest away from the surface cannot be seen at all. In this case, the target markers 66 are generally bead-shaped, comprising a liquid NMR contrast agent encapsulated by a plastic hull. The plastic hull was painted on the outside with a black permanent marker to allow for light absorption for the PAI purposes.

FIG. 28 shows the fused or co-registered PA and NMR images. The light, approximately spherical objects are a representation of the NMR contrast agent in the NMR image. The shape of the beads in the NMR image is not precisely spherical, because due to the simple manufacture, the inner volume of the hull encapsulating the NMR contrast agent is not precisely spherical, but has bulged portions that can be seen in the image of FIG. 28. The dark objects correspond to the PA images, and it is seen that the PA image is indeed correctly registered with the NMR image. It was seen that in the first experiment carried out, without any optimization, a target registration error of 2.0 mm at a fiducial registration error of 0.4 mm could be obtained.

Note that in the image of FIG. 28, the regions of high PAI signal seem to "soar" above the NMR representations of the NMR contrast agent. This is understandable, since the PAI signal is due to absorption of light by the black marker ink provided at the outer surface of the hulls encapsulating the NMR, while the NMR contrast agent is separated from this ink layer by the thickness of the hull.

Moreover, it is seen that the PAI signal generated from region of the surface of the target marker 66 hull close to the upper surface of the phantom, from where the PA images are recorded, is much stronger than the signal generated from the black ink on other portions of the surface of the hull, and in particular the surface facing away from the upper surface of the phantom. This is due to the fact that excitation light is irradiated from the top surface of the phantom, and that most of the excitation light is absorbed from the black ink at the upper portion of the target marker 66 (i.e. the portion facing the upper surface of the phantom), so that the light fluence in the remaining regions of the surface of the hull is reduced, leading to a much weaker PA signal. This effect will be referred to as a "shadowing" effect for short in the following. Also, it is seen that the PAI signals associated with target markers 66 further away from the upper surface of the phantom are likewise considerably reduced, since again, in deeper layers, the light fluence is weaker.

These effects can in practice be accounted for in various manners. In particular, in practical applications, one can approximately assess or estimate the optical fluence in a certain region of the PAI volume and calibrate the PAI signal accordingly, to therefore account for regions of reduced fluence. The shadowing effect can in practice be mitigated by irradiating the excitation light from different directions. However, in various embodiments, this will not be necessary, since in many cases, images including the relevant information from a clinical point of view can often be obtained with "incomplete" PA images, i.e. images suffering from shadowing effects or reduced PA intensities in regions of lower light fluence.

To further appreciate this, reference is made to FIGS. 29 and 30, showing for comparison a PA image (FIG. 29) and an US image (FIG. 30) of the same volume next to each other. Also shown in the figures by a broken line is the location of a vessel. It is seen that in the US image, the entire volume of the vessel can be discerned, while in the PA image, due to the aforementioned shadowing effect, the large PA signal is concentrated at the top region of the vessel, which in FIG. 31 is schematically shown at reference sign 68. However, from the upper region 68 of the vessel as represented in the PA image alone, knowing the typical shape of vessels, it is of course possible to predict the shape and size of the total vessel (again indicated by the dashed line). The "remainder of the vessel", i.e. the portion of the predicted vessel outside the region 68 of strong PA signal can hence also be predicted as being part of the vessel—this "remainder of the vessel" is designated by reference sign 70 in FIG. 31.

In other words, although the PA signal is too weak to make a clear distinction in all portions of the vessel from the PA signal per se, it is nevertheless possible to label each of the pixels within the remainder of the vessel 70 to be part of the vessel as well. This labelling of pixels with a corresponding class of what is being represented is also known as "semantic segmentation". In the example shown, the corresponding "class of what is being represented" would in the simplest case be whether the pixel is part of a vessel or not.

In preferred embodiments, the PAI image is used for obtaining a semantic representation of the imaged volume. Herein, semantic representation involves an understanding of each pixel of the PAI image with regard to high-level semantics, e.g. spatial, functional and semantic relations. This is schematically illustrated in FIG. 32, where from the PAI image, a semantic representation is generated, in which for the pixels associated with a vessel region illustrated in FIG. 32, high-level semantics beyond the mere PA signal value is obtained, for example that the respective pixels correspond to a vessel, that the vessel is an artery, that the present oxygenation is 99%, that the radius of the vessel at this location is 5 mm and so forth. Further high-level semantics could involve the flow direction of blood within the vessel, or information with regard to the hierarchical position of the vessel as a branch in a vessel tree and the like. The latter information could also include the connectivity between various vessels within the PAI volume, for example to determine which of the subbranches of a vessel tree would be affected if a certain vessel was clamped or clogged.

As mentioned before, the PAI method has at least two important practical advantages, one being the relatively easy and quick way of obtaining the images, with comparatively cheap imaging equipment (in particular when only 2D images are recorded), the other being the capability of assessing functional parameters, in particular functional parameters relying on molecular information of the imaged region. These advantages can be exploited particularly well if the PA image is used for generating a semantic representation of the volume, as should have become apparent from the examples given above. For example, with reference to the example of a vessel tree, it is possible to quickly assess oxygenation within part of the vessel tree, and in case of low oxygenation, immediately identify subordinate vessel branches that will then likewise be affected by reduced oxygen supply.

In order to construct the semantic representation of the PAI volume, it may be helpful to have additional information derived from other imaging modalities, in particular those that are less affected by the inherent limitation of the PA method, such as limited fluence in deeper layers and shadowing effects. In some embodiments, additional information can be supplied by US images, which can typically be easily obtained with the same apparatus, as explained above. In other embodiments, this additional information can be obtained from other imaging modalities, in particular CT or NMR imaging, which are particularly suitable for providing high-resolution and detailed anatomical or morphological information.

However, the inventors noticed that in other embodiments, the semantic representation may be generated based on the PAI images alone, when using a machine learning algorithm that has e.g. been trained based on PAI images in combination with co-registered images of other imaging modalities. In this case, the anatomical information derived from co-registered images obtained with different imaging modalities can be used as ground truth during the machine learning. In addition or alternatively, the machine learning algorithm may be trained using simulated PA volumes, where the exact tissue topology underlying the simulation serves as ground truth.

Preferred machine learning algorithms for this purpose are supervised deep learning-based convolutional neural networks, that are specifically suitable for image analysis due to the incorporation of spatial image context while leveraging a reduced number of learnable free parameters. A particularly suitable network for the purposes of this embodiment is the U-Net as described in Ronneberger, et al. "*U-net: Convolutional networks for biomedical image segmentation.*" *International Conference on Medical image computing and computer-assisted intervention. Springer, Cham,* 2015, and in Isensee, et al. "*nnU-Net: a self-configuring method for deep learning-based biomedical image segmentation.*" *Nature methods* 18.2 (2021): 203-211. However, other machine learning-based methods could be applied, for example leveraging principles of generative adversarial neural networks (GAN), as e.g. described in Goodfellow, et al. "*Generative adversarial networks.*" *Communications of the ACM* 63.11 (2020): 139-144. One approach could be to use the PA image as condition to generate semantic segmentations or to incorporate adverserial loss functions in above mentioned convolutional approaches, in a manner generally described in L Luc, Pauline, et al. "*Semantic segmentation using adversarial networks.*" *arXiv preprint arXiv:*1611.08408 (2016).

While the present invention has been described in terms of specific embodiments, it is understood that variations and modifications will occur to those in the art, all of which are intended as aspects of the present invention. Accordingly, only such limitations as appear in the claims should be placed on the invention.

REFERENCE SIGNS

- 10 PAI imaging system
- 12 PAI probe
- 14 control device
- 15 inertial measurement unit
- 16 light source
- 18 biological tissue
- 20 tissue-imaging light pulse
- 22 pressure wave
- 24 transducer
- 26 piezoelectric transducer element
- 28 two-dimensional optical pattern
- 30 pattern-imaging light pulse
- 32 ultrasound pulse
- 34 forearm
- 36 vessel
- 38 imaging plane
- 40 three-dimensional optical pattern
- 42 upper pattern plane
- 44 lower pattern plane
- 45 plastic foil
- 46 2D-PAI image
- 48 two-dimensional section plane
- 50 gel pad with optical pattern
- 52 upper side of gel pad 50
- 54 lower side of gel pad 50
- 56 collar
- 58 MRI contrast agent
- 60 radiopaque marker
- 62 visible grid
- 64 pen for drawing optical pattern
- 66 target marker

What is claimed is:

1. A method of photoacoustic imaging (PAI) or ultrasound (US) imaging of biological tissue, said method comprising:

recording one or both of two-dimensional (2D)-PAI and/ or US images of said biological tissue, each of said 2D-PAI or US image being associated with a corresponding image plane, wherein said method further comprises providing, prior to recording said 2D-PAI or US images of said biological tissue, an optical pattern on or close to a surface of said biological tissue, said optical pattern comprising one or more optical dyes configured for absorbing light at a pattern-characteristic wavelength, and wherein said 2D-PAI images are recorded using pattern-imaging light pulses having a-said pattern-characteristic wavelength for which the absorption by said one or more dyes is sufficiently high such that said optical pattern is visibly represented in said 2D-PAI images, wherein said optical pattern is configured such that a location of said image plane with respect to said optical pattern can be determined from a representation of said optical pattern in said 2D-PAI image or such that a relative location of the respective image planes of consecutively recorded 2D-PAI images with respect to each other can be determined, or both, wherein said method further comprises determining one or both of said location of said image plane of each given 2D-PAI or US image among said recorded 2D-PAI and/or US images of said biological tissue with respect to said optical pattern, and said relative location of the respective image planes of consecutively recorded 2D-PAI or US images among said recorded 2D-PAI and/or US images from said representation of said optical pattern in said given 2D-PAI images, or in one or more 2D-PAI images recorded while a PAI probe is in a same position or a position close to the position in which said given 2D-PAI or US image(s) of said biological tissue is recorded.

2. The method of claim 1, wherein recording said 2D-PAI images of said biological tissue comprises irradiating tissue-imaging light pulses into said biological tissue using said PAI probe, said tissue-imaging light pulses having tissue-characteristic wavelengths to be absorbed in said biological tissue, receiving pressure waves generated upon absorption of said tissue-imaging light pulses in said biological tissue using said PAI probe and converting said received pressure waves into electrical signals, and constructing said 2D-PAI images from said electrical signals, said 2D-PAI images representing a space-resolved absorption of said tissue imaging-light pulses in a sectional image plane within said biological tissue.

3. The method of claim 2, wherein an absorptivity of the of the one or more dyes at said pattern-characteristic wavelength is at least a factor of two higher than at said tissue-characteristic wavelengths.

4. The method of claim 1, wherein said determined location of the image plane of said given 2D-PAI/US image among said recorded 2D-PAI and/or US images is used for one or more of constructing a three-dimensional (3D) image from a plurality of 2D-PAI/US images among said recorded 2D-PAI and/or US images, targeting a specific anatomical location at a first point in time and re-targeting said specific anatomical location at a second point in time different from said first point in time, and registering said given 2D-PAI/US image among said recorded 2D-PAI and/or US images with imaging data obtained with another imaging modality.

5. The method of claim 1, wherein said optical pattern extends in at least one two-dimensional pattern plane, wherein said determining the location of the image plane of each said given 2D-PAI/US image among said recorded 2D-PAI and/or US images of said biological tissue with respect to said optical pattern comprises determining a sectional line along which said image plane of said given 2D-PAI/US image and said two-dimensional pattern plane intersect with each other.

6. The method of claim 5, wherein said PAI probe is placed on the surface of said biological tissue such that a corresponding 2D-PAI/US image plane is perpendicular to said two-dimensional pattern plane.

7. The method of claim 1, wherein said optical pattern has a three-dimensional structure, extending in at least one two-dimensional pattern plane and additionally in a thickness direction perpendicular to said two-dimensional pattern plane, wherein said determining the location of the image plane of each said given 2D-PAI/US image among said recorded 2D-PAI and/or US images of said biological tissue with respect to said optical pattern amounts to determining a sectional plane along which said image plane of said given 2D-PAI/US image and said three-dimensional structure intersect with each other.

8. The method of claim 7, wherein said optical pattern extends in two or more two-dimensional pattern planes, which are spaced from each other in thickness direction, wherein said determining the location of the image plane of each said given 2D-PAI/US image among said recorded 2D-PAI and/or US images of said biological tissue with respect to said optical pattern comprises determining a sectional line along which said image plane of said given 2D-PAI/US image and one of said two or more two-dimensional pattern planes intersect with each other, as well as a step of determining an angle between said one of the two or more two-dimensional pattern plane and said image plane of said given 2D-PAI/US image of said biological tissue based on at least one other of said two or more two dimensional pattern planes.

9. The method of claim 1, wherein said optical pattern comprises three or more lines generally extending along an extension direction, but also diverging in said extension direction.

10. The method of claim 9, wherein said recording 2D-PAI/US images comprises moving said PAI probe along said extension direction and recording said 2D-PAI/US images at different positions along said extension direction.

11. The method of claim 10, wherein said step of determining the location of the image plane of each said given 2D-PAI/US image among said recorded 2D-PAI and/or US images of said biological tissue with respect to said optical pattern comprises determining a position along said extension direction based on distances between representations of said three or more lines, and in particular based on a sum or an average of said distances between representations of said three or more lines in said given 2D-PAI image among said recorded 2D-PAI images, or in the one or more 2D-PAI images recorded while said PAI probe is in the same position or a position close to the position in which said given 2D-PAI/US image among said recorded 2D-PAI and/or US images of said biological tissue is recorded.

12. The method of claim 11, further comprising a step of determining an angle between said extension direction and a sectional line of the image plane with a pattern plane in which said three or more lines are arranged, based on distances between presentations of said three or more lines, and in particular based on a difference or quotient of distances between representations of said three or more lines in said given 2D-PAI image among said recorded 2D-PAI images, or in the one or more 2D-PAI images recorded while said PAI probe is in the same position or a position close to the position in which said given 2D-PAI/US image among said recorded 2D-PAI and/or US images of said biological tissue is recorded.

13. The method of claim 12, wherein said optical pattern is provided on or in a foil or a cushion or pad to be placed on top of said biological tissue.

14. The method of claim 13, wherein said cushion or pad has a lower side adapted to or capable of adapting to the surface of said biological tissue and an upper side having a flat surface for placing said PAI probe thereon.

15. The method of claim 1, wherein said optical pattern is initially provided on a carrier and wherein said method comprises a step of transferring said optical pattern from said carrier to said surface of said biological tissue.

16. The method according to claim 1, wherein for recording said 2D-PAI images of said biological tissue, at least four different tissue-characteristic wavelengths are used.

17. The method of claim 16, wherein said optical dye is visible in a visible light spectrum.

18. The method according to claim 1, wherein the method further comprises using said optical pattern as a calibration standard for normalizing PAI intensity values.

19. The method of claim 1, wherein said step of providing said optical pattern on or close to said surface of said biological tissue comprises drawing said optical pattern on the surface of the biological tissue or on a carrier arranged close to said surface of said biological tissue, wherein said method further comprises a step of taking a photograph of the drawn optical pattern and using information derived from said photograph in one or both of said determining the location of the image plane of each said given 2D-PAI or US image among said recorded 2D-PAI and/or US images of said biological tissue with respect to the drawn optical pattern, and said determining the relative location of the respective image planes of consecutively recorded 2D-PAI or US images among said recorded 2D-PAI and/or US images.

20. The method of claim 1, wherein said step of determining said relative location of the respective image planes of consecutively recorded 2D-PAI or US images among said recorded 2D-PAI and/or US images involves employing a continuity constraint on the representation of said optical pattern in said consecutively recorded 2D-PAI images, or in 2D-PAI images recorded while said PAI probe is in the same position or a position close to the positions in which the respective consecutive US images of said biological tissue are recorded.

21. The method of claim 1, wherein regions within said optical pattern are encoded by one or both of
    using, as said one or more optical dyes, dyes having absorption maxima at different pattern-characteristic wavelengths for different regions within said optical pattern, and
    a visible grid or other type of visible pattern allowing for identifying regions within said optical pattern by visual inspection.

22. The method of claim 21, wherein an absorptivity of a pigment or dye used for forming said visible grid or other type of visible pattern at said tissue-characteristic wavelengths is sufficiently low such that said visible grid or other type of visible pattern is substantially not present in said 2D-PAI images.

23. A system for one or both of photoacoustic imaging (PAI) and ultrasound (US) imaging of biological tissue using a PAI probe,
    said PAI probe comprising a detection device for receiving pressure waves generated upon absorption of tissue-imaging light pulses, and optionally also ultrasonic waves employed in an additional US imaging mode, and converting said received pressure waves into electrical signals,
wherein said system further comprises a control device for constructing two-dimensional (2D)-PAI or US images from said electrical signals, wherein each said 2D-PAI or US image is associated with a corresponding image plane,
wherein said system further comprises means for providing an optical pattern on or close to the surface of said biological tissue, said optical pattern comprising one or more optical dyes configured for absorbing light at a pattern-characteristic wavelength, wherein said PAI probe is further configured to provide pattern-imaging light pulses having a pattern-characteristic wavelength for which the absorption by said one or more dyes is sufficiently high such that said optical pattern is visible in said 2D-PAI image obtained with said PAI probe when employing said pattern-imaging light pulses,
wherein said optical pattern allows for determining a location of said image plane with respect to said optical pattern from a representation of the optical pattern in said 2D-PAI image or for determining a relative location of the respective image planes of consecutively recorded 2D PAI-images with respect to each other, or both,
wherein said control device is further configured for determining one or both of
    the location of said image plane of each given 2D PAI or US image among said 2D-PAI and/or US images of said biological tissue with respect to said optical pattern, and
    said relative location of the respective image planes of consecutively recorded 2D-PAI or US images among said 2D-PAI and/or US images
from said representation of said optical pattern in said given 2D-PAI images or in one or more 2D-PAI images recorded while said PAI probe is in a same position or a position close to the position in which said given 2D-PAI images or US images of said biological tissue is recorded.

24. The system of claim 23, wherein the system comprises at least one light source for providing tissue-imaging light pulses having one or more tissue-characteristic wavelengths to be absorbed in said biological tissue, wherein said system is configured for recording said 2D-PAI images of said biological tissue by
    irradiating, using said at least one light source, tissue-imaging light pulses into said biological tissue using said PAI probe, said tissue-imaging light pulses having tissue-characteristic wavelengths to be absorbed in said biological tissue,
    receiving, using said detection device, pressure waves generated upon absorption of said tissue-imaging light pulses in said tissue using said PAI probe and converting said received pressure waves into electrical signals, and
    constructing, using said control device, said 2D-PAI images from said electrical signals, said 2D-PAI images representing a space-resolved absorption of said tissue imaging-light pulses in a sectional image plane within said biological tissue.

25. The system of claim 24, wherein an absorptivity of the of the one or more dyes at said pattern-characteristic wavelength is at least a factor of two higher than at said tissue-characteristic wavelengths.

26. The system of claim 23, wherein said control device is further configured for using said determined location of the image plane of said given 2D-PAI/US image among said 2D-PAI and/or US images for one or more of constructing a three-dimensional (3D) image from a plurality of 2D-PAI/US images among said 2D-PAI and/or US images, targeting a specific anatomical location at a first point in time and re-targeting said specific anatomical location at a second point in time different from said first point in time, and registering said given 2D-PAI/US image among said 2D-PAI and/or US images with imaging data obtained with another imaging modality.

27. The system of claim 23, wherein said optical pattern extends in at least one two-dimensional pattern plane, wherein the control device is configured for determining said location of the image plane of each said given 2D-PAI/US image among said 2D-PAI and/or US images of said biological tissue with respect to said optical pattern at least in part by determining a sectional line along which said image plane of said given 2D-PAI/US image and said two-dimensional pattern plane intersect with each other.

28. The system of claim 23, wherein said PAI probe is configured to be placed on the surface of said biological tissue such that a corresponding 2D-PAI/US image plane is perpendicular to said two-dimensional pattern plane.

29. The system of claim 23, wherein said optical pattern comprises three or more lines generally extending along an extension direction, but also diverging in said extension direction.

30. The system of claim 29, wherein said PAI probe is configured for recording 2D-PAI/US images while moving said PAI probe along said extension direction and recording said 2D-PAI/US images at different positions along said extension direction.

31. The system of claim 30, wherein said control device is configured for determining the location of the image plane of each said given 2D-PAI/US image among said 2D-PAI and/or US images of said biological tissue with respect to said optical pattern at least in part by determining a position along said extension direction based on distances between representations of said three or more lines, and in particular based on a sum or an average of said distances between representations of said lines in said given 2D-PAI image among said 2D-PAI images, or in the one or more 2D-PAI images recorded while said PAI probe is in the same position or a position close to the position in which said given 2D-PAI/US image among said 2D-PAI and/or US images of said biological tissue is recorded.

32. The system of claim 31, wherein said control device is further configured for determining an angle between said extension direction and a sectional line of the image plane with a pattern plane in which said three or more lines are arranged, based on distances between presentations of said three or more lines, and in particular based on a difference or quotient of distances between representations of said three or more lines in said given 2D-PAI image among said 2D-PAI images, or in the one or more 2D-PAI images recorded while said PAI probe is in the same position or a position close to the position in which said given 2D-PAI/US image among said 2D-PAI and/or US images of said biological tissue is recorded.

33. The system of claim 23, wherein said means for providing said optical pattern comprises a foil or a cushion or a pad on which said optical pattern is provided and which is to be placed on top of said biological tissue.

34. The system of claim 33, wherein said cushion or pad has a lower side adapted to or capable of adapting to the surface of said biological tissue and an upper side having a flat surface for placing a said PAI probe thereon.

35. The system of claim 23, wherein said means for providing said optical pattern comprises a carrier on which said optical pattern is initially provided, wherein said optical pattern is suitable for being transferred from said carrier to said surface of said biological tissue, in particular to the skin of a body part.

36. The system of claim 23, wherein said at least one light source is configured for providing at least four different tissue-characteristic wavelengths.

37. The system of claim 23, wherein the dye is visible in a visible light spectrum.

38. The system of claim 23, wherein said means for providing said optical pattern is a pen for drawing said optical pattern on the surface of the biological tissue or on a carrier arranged close to said surface of said biological tissue, and wherein said control device is further configured for using information derived from a photograph taken of said drawn optical pattern in said determining the location of the image plane of each said given 2D-PAI or US image among said 2D-PAI and/or US images of said biological tissue with respect to the optical pattern drawn with said pen, or in the determining said relative location of the respective image planes of consecutively recorded 2D-PAI or US images among said 2D-PAI and/or US images.

39. The system of claim 23, wherein said control device is configured for determining said relative location of the respective image planes of consecutively recorded 2D-PAI or US images among said recorded 2D-PAI and/or US images employing a continuity constraint on the representation of said optical pattern in said consecutively recorded 2D-PAI images, or in 2D-PAI images recorded while said PAI probe is in the same position or a position close to the positions in which the respective consecutive US images of said biological tissue are recorded or configured for estimating a speed of a movement of said PAI probe with respect to said biological tissue based on a difference in said representation of said optical pattern in said consecutively taken 2D-PAI images.

40. The system of claim 23, wherein regions within said optical pattern are encoded by one or both of said optical dyes having absorption maxima at different pattern-characteristic wavelengths for different regions within said optical pattern, and a visible grid or other type of visible pattern allowing for identifying regions within said optical pattern by visual inspection.

* * * * *